United States Patent [19]

Ionnou et al.

[11] 4,245,646
[45] Jan. 20, 1981

[54] NUCLEAR CARDIOLOGY APPARATUS AND METHOD

[75] Inventors: Basil N. Ionnou, North Haven; Donald S. Kearns, Farmington; Robert J. Applegate, Wallingford; Richard M. Sano, Stamford; Edward K. Prokop, Wallingford, all of Conn.

[73] Assignee: Picker Corporation, Cleveland, Ohio

[21] Appl. No.: 917,063

[22] Filed: Jun. 19, 1978

[51] Int. Cl.³ .............................................. A61B 5/02
[52] U.S. Cl. ................................. 128/653; 250/363 S
[58] Field of Search ...................... 128/653, 659–663; 250/362 S

[56] References Cited

U.S. PATENT DOCUMENTS

| 3,670,715 | 6/1972 | Perilhou | 250/106 T |
|---|---|---|---|
| 4,033,335 | 7/1977 | Nickles | 128/659 |
| 4,101,961 | 7/1978 | Reiber | 128/633 |
| 4,111,191 | 9/1978 | Shaw | 128/659 |
| 4,126,785 | 9/1978 | Hounsfield | 250/445 T |

FOREIGN PATENT DOCUMENTS

| 2617886 | 5/1977 | Fed. Rep. of Germany | 128/659 |
|---|---|---|---|
| 562120 | 12/1977 | U.S.S.R. | 128/659 |

OTHER PUBLICATIONS

Sano, R. et al., "Cardiac Stroke Volume Measured Using a Scintillation Camera with Data Processor," Jrnl. Nuc. Med. Jun. 1969, Abstracts.
Sano, R. et al., "A Nuclear Cardiology Module for Angle Cameras", SNM 24th Annual MTG, Instr. 2: Poster Session, Jun. 24, 1977.
Willson, K. et al., "Ditigal Processing of UTS Cardiac Images," Conf: Proc. Zd. Europ. Cong. on UTS in Med., Munich 12-16 May, 1975, pp. 103-107.
DeJong, L. et al., "Aut. Det. of LV Outline in Angiographs Using T.V. Signal Proc. Tech.", IEEE/BME Trans. vol. BME-22, No. 3, May 1975.

*Primary Examiner*—Robert W. Michell
*Assistant Examiner*—Francis J. Jaworski
*Attorney, Agent, or Firm*—Watts, Hoffmann, Fisher & Heinke Co.

[57] ABSTRACT

A nuclear cardiology system for use with a scintillation camera for evaluating cardiac function by real time measurement of the variation of radiation from the heart of a patient to whom is administered a radioactive tracer. The camera provides data describing the location of individual counts representing radiation events coming from the patient. The system segregates, in real time, counts corresponding to radiation from an electronically defined region of interest describing an investigated part of the heart, such as the left ventricle. Synchronized by the patient's electrocardiogram, time gated memory circuitry divides each heartbeat into a series of subintervals, and stores indications of the respective amounts of radiation events emanating from the region of interest during each of the subintervals. Calculating circuitry scans the stored information and, based on the maximum and minimum respective radiation amounts detected in the subintervals, computes the fraction of blood ejected by the heart in each beat. A strip chart recorder provides a permanent representation of the curve of radiation from the region of interest, as defined by the indicated series of subinterval radiation amounts.

36 Claims, 37 Drawing Figures

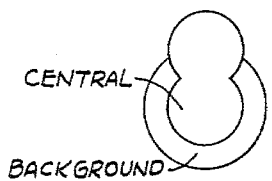
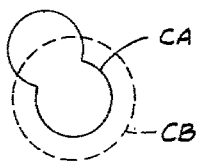
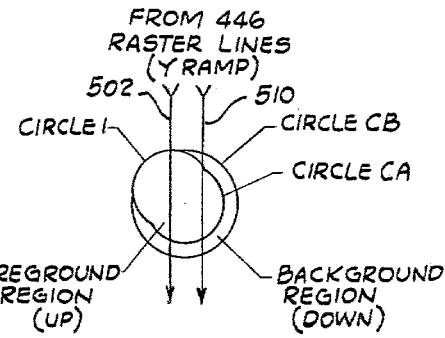
Fig.11  Fig.12  Fig.13
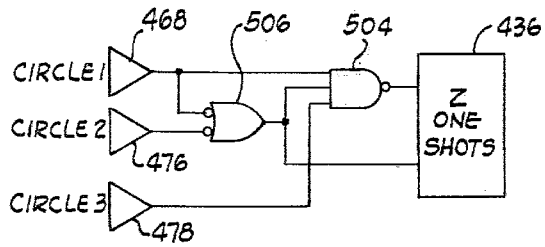
Fig.14
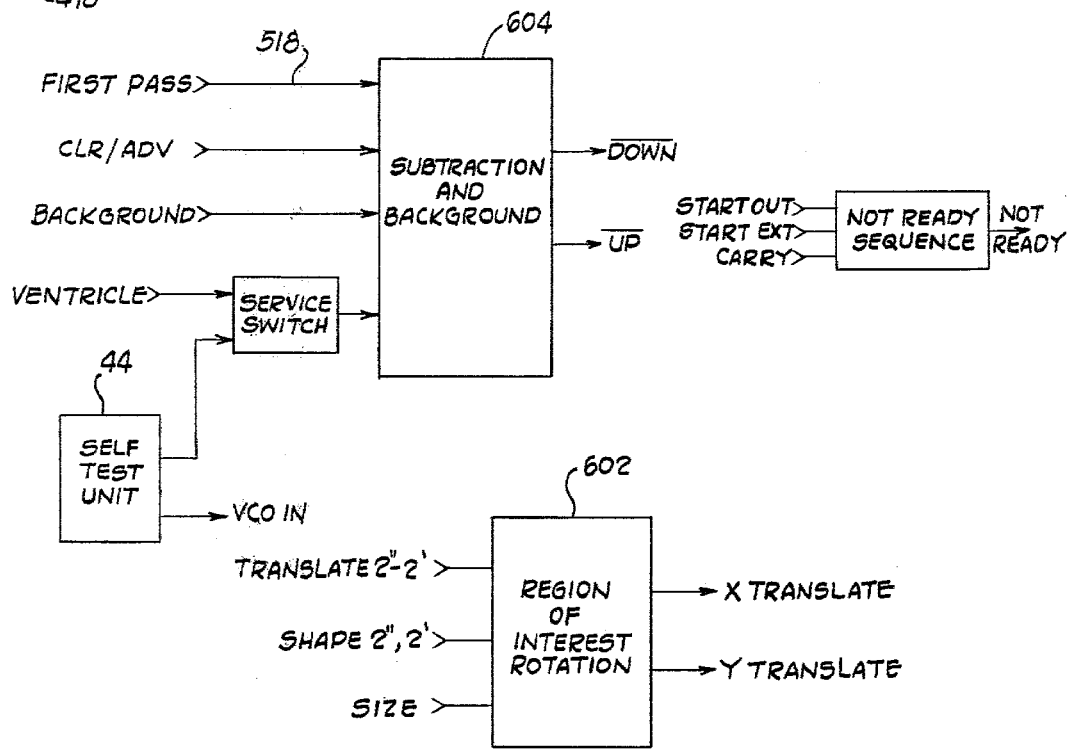
Fig.15
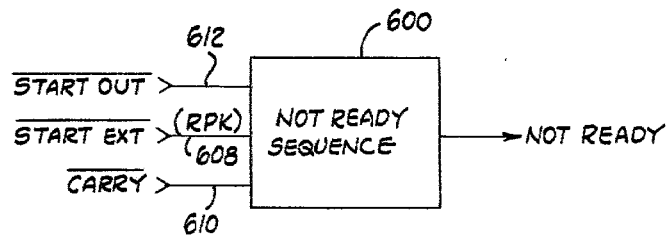
Fig.16

NUCLEAR CARDIOLOGY APPARATUS AND METHOD

BACKGROUND OF THE INVENTION

1. Field of the Invention

This invention relates to the field of nuclear cardiology in medical diagnosis. In nuclear cardiology, a patient's heart function is evaluated by monitoring of radiation from, one for example, heart chamber, following the administration of a radioactive tracer into the patient's cardiovascular system. A scintillation camera is used to detect, and indicate location of, radiation events within the patient's heart caused by the presence of the tracer in his blood.

Data processing apparatus is used to develop information regarding the patient's cardiac function from the pattern of variation of radioactivity from the inspected region of interest, which may, for example, be selected as defining the patient's left ventricle. This time varying pattern of radiation describes volumetric time variation of blood in the inspected chamber. From this information, a curve describing the chamber's time varying volume can be derived. Calculations incorporating the minimum and maximum volume can be made which describe the fraction of blood within the chamber which is pumped by the heart in the course of each beat. Specifically, the ejection fraction, or $$E.F. = D - S/D$$

where D is the end diastolic volume of the heart chamber and S is the end systolic heart chamber volume.

2. Description of the Prior Art

It has been proposed to implement the above described nuclear cardiology diagnostic technique by the use of an electronic data processing computer in conjunction with a scintillation camera and an electrocardiogram apparatus. In accordance with this proposal, an investigator injects a quantity of radioactive tracer material into the patient's cardiovascular system. When the radioactive tracer material has reached the heart, analog signals from the scintillation camera, indicating the location of nuclear radiation events within the patient's body over a time period, are digitized. This digitized location information is recorded in its entirety in the computer memory. The computer is programmed to subsequently scan this information, and to isolate therefrom information describing radiation events emanating from a particular zone of the patient's body.

The computer of such a proposed system is programmed to analyze the selected data from the predetermined zone to derive information relating to heart function. In doing this, the computer subdivides the stored information into a series of portions, each portion corresponding to radiation occurring during a particular time segment. The information, thus time divided, is then analyzed by computational manipulations of the computer to produce a representation of a curve describing the time varying volume of radioactively traced blood in the studied heart chamber.

While such a system affords utility in medical diagnostic examinations, it requires highly complex and expensive apparatus for operation. The requirement for an electronic data processing computer is an obvious example of this very considerable expense the complexity. The computer must have sufficient memory capability to incorporate a large amount of stored information. The proposed system must store the entirety of radiation location indicating information prior to the beginning of analysis upon it. This slows system operations since it requires analysis of the stored data to await the completion of the storage operation before it can proceed.

Accordingly, there has existed a desire for a relatively simple and inexpensive system for performing specific diagnostic routines in nuclear cardiology, such as ejection fraction calculation, left ventricular ejection time, and left ventricle integrated time activity curve analysis.

SUMMARY OF THE INVENTION

This invention overcomes the disadvantages of prior art systems by providing a system and method for performing cardiac function evaluations accomplished by the computer dependent system described above, without much of the expense and complexity of apparatus required by that system.

Apparatus incorporating this invention includes a cardiac function evaluating system responsive to radiation events produced by a radioactive tracer in a patient's cardiovascular system. The system is designed for use with a radiation detector, such as a scintillation camera, which produces data describing radiation distribution of the tracer in the subject's body.

The system includes circuitry for electrically segregating that data produced by the detector in response to radiation events occurring within a predetermined region of interest. The region of interest preferably defines a portion of the subject's heart, such as the left ventricle. The electrical segregation is executed in real time, relative to the production of the radiation event counts, i.e., on a count by count basis.

The system also includes time gated multichannel memory circuitry, for processing the segregated data from subintervals of the patient's heartbeat cycle, synchronous with the patient's electrocardiogram, for describing a cardiac function, and a display apparatus which is responsive to the memory circuitry for producing an indication of a characteristic of the heart function being evaluated.

An important feature of this invention is that the initial segregation of data representing radiation within the region of interest is performed in real time. This real time data segregation eliminates the necessity for storing the entirety of position indicating data produced by the camera detector, as had been necessary in the previous computer systems. Such prior systems went about the function of segregating the data only subsequent to the data storage.

Employment of a real time segregation technique eliminates the previous need for storing the entirety of the information before segregation, (including the precise indications of position within the region of interest) and accordingly eliminates the need for sophisticated digital memory formerly needed for this purpose. Also eliminated is the need for computerized scanning of the stored information to accomplish the selection of data corresponding to the region of interest.

Rather than storing in a complicated digital memory, in a form describing positional location of each count, the counts are merely evaluated immediately as to whether they correspond to region of interest radiation. Those counts which do correspond to the region of interest are simply counted, and the number stored in a simple multichannel time gated memory circuit, without regard to where, in the region of interest, they originated.

This system thus simplifies the apparatus required, in that the only test performed on each count is whether it came from a region of interest, there being no further need to retain or deal with (1) any positional information relating to the region of the interest counts, or (2) any information relating to events outside the region.

A more specific aspect of the invention involves the time gated memory circuitry comprising circuitry for describing a curve representing the time variation of the quantity of blood within the investigated portion of the subject's heart.

In accordance with this feature, the memory circuitry divides the subject's heartbeat into a series of time subintervals, and defines the curve by a sequence of accumulated radiation count totals, each of the totals corresponding to one of the series of subintervals within the subject's heartbeat cycle.

Another specific feature of the invention is the provision of means for adjusting the duration and number of the subintervals into which the heartbeat cycle is divided. This enables variation in a tradeoff between speed of execution of the selected cardiac evaluation protocol and the fineness of definition of the volumetric curve.

In accordance with another specific aspect, the data segregation circuitry defines two regions of interest. One region of interest is a central region of interest superimposed over the investigated portion of the subject's heart. The other region of interest is locatable to enable the separate segregation of background radiation. In accordance with this specific feature, there is also provided circuitry for subtracting the radiation detected in the background region of interest from that detected in the central region. This feature eliminates error which would otherwise result from detection of background information in the central region of interest.

A still further specific feature of the invention is the provision of circuit means for adjusting the size, relative position and orientation and shape of a region of interest.

Other circuitry is employed to discard a portion of the information representing the last 25% of the beat cycle, in recognition of the fact that this information can skew the evaluation undesirably.

This invention will be understood in detail by reference to the following detailed description, and to the drawings, in which:

DESCRIPTION OF THE DRAWINGS

FIGS. 12 and 13 show further region of interest illustrations;

FIG. 14 is a detailed block diagram showing a suporportion of the portion of the system shown in FIG. 2;

FIG. 15 is a block diagram illustrating another subportion of the system shown in FIG. 2;

FIG. 16 is a detailed block diagram illustrating a portion of the system of FIG. 2;

DESCRIPTION OF THE PREFERRED EMBODIMENT GENERAL SYSTEM

Figure 1:
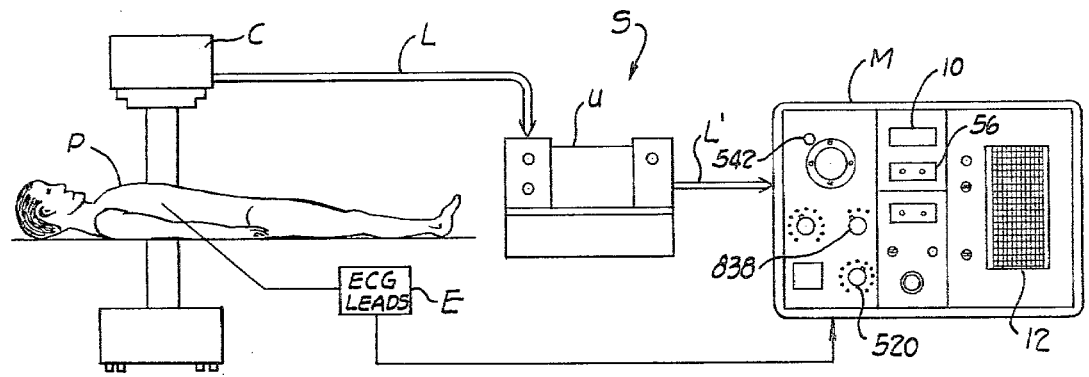
FIG. 1 is a graphical illustration of a system incorporating the present invention.

FIG. 1 is a graphical illustration of a nuclear cardiology system S incorporating the present invention. The system S detects radiation emanating from the heart of a patent P and resulting from a previous administration of the patient with a radioactive isotope tracer. The tracer is administered into the bloodstream of the patient, and, after it reaches his hart, the radiation is detected. A radiation camera C, in response to the emitted radiation, produces electrical signals indicating the location, on an X–Y plane, of each sensed radiation event. The electrical signals are transmitted over a set of leads L to an operations control unit U. Components in the unit U process the electrical signals transmitted over the leads L to present a visual representation of the pattern of radiation emanating from the patient within the field of view of the camera C. Electrical signals representing the X–Y parameters of the radiation events sensed by the camera C are transmitted over another set of leads L' to a cardiac module unit M. The cardiac module M also receives electrocardiogram signals through electrocardiogram electrodes E connected to the patient to sense electrical impulses from the patient's heart.

In response to the electrocardiogram signal and the X–Y coordinate signals, from the camera, the cardiac module M produces a digital readout of the ejection fraction of blood from a poriton of the patient's heart such as the left ventricle. This digital readout appears on an LED (light emitting diode) visual output panel 10. The cardiac module M also produces a graphical representation of the time variation of blood volume in the patient's left ventricle on a strip chart recorder 12.

The nuclear camera C is suitably a nuclear camera designated "Dyna Camera 4" manufactured by Picker Corporation, Northford, Connecticut, U.S.A. The control unit U is also a portion of the Dyna Camera 4. The electrocardiogram electrodes E may be any type of suitable ECG leads, such as a Model S3300, manufactured by Andover Medical, Inc.

The cardiac module M is an apparatus that cooperates with the nuclear camera C to evaluate heart function noninvasively, particularly left ventricle performance. The module M synchronizes on the electrocardiogram signal from the patient, gates the information regarding nuclear event occurrence and location from the camera C and performs two general functions.

Figure 1A:
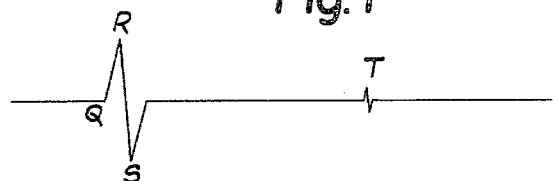
FIG. 1A is a graphical representation of a human electrocardiogram cycle.

The module M divides the QRS complex interval of the patient's ECG heartbeat function (illustrated in FIG. 1A) into a predetermined number of subintervals, i.e., up to 256. The module M gates, accumulates and stores the number of radiation events sensed by the camera which occur within a region of interest defining the left ventricle, and calculates the ejection fraction output by the patient's ventricle during his heartbeat cycle. The ejection fraction is defined as: $D-S/D$, where D is the blood volume at the end diastolic portion of the patient's heartbeat and S is the blood volume at the end systolic point of the heartbeat cycle. (See e.g., the ventricular volume plot in FIG. 6).

The cardiac module M also prints out, on a strip chart recorder 12, the electrocardiogram profile of the patient's heartbeat, and a representation of the time variation of the radioactivity in the left ventricle during the heartbeat cycle, in synchronism with the electrocardiogram signal.

Figure 2:
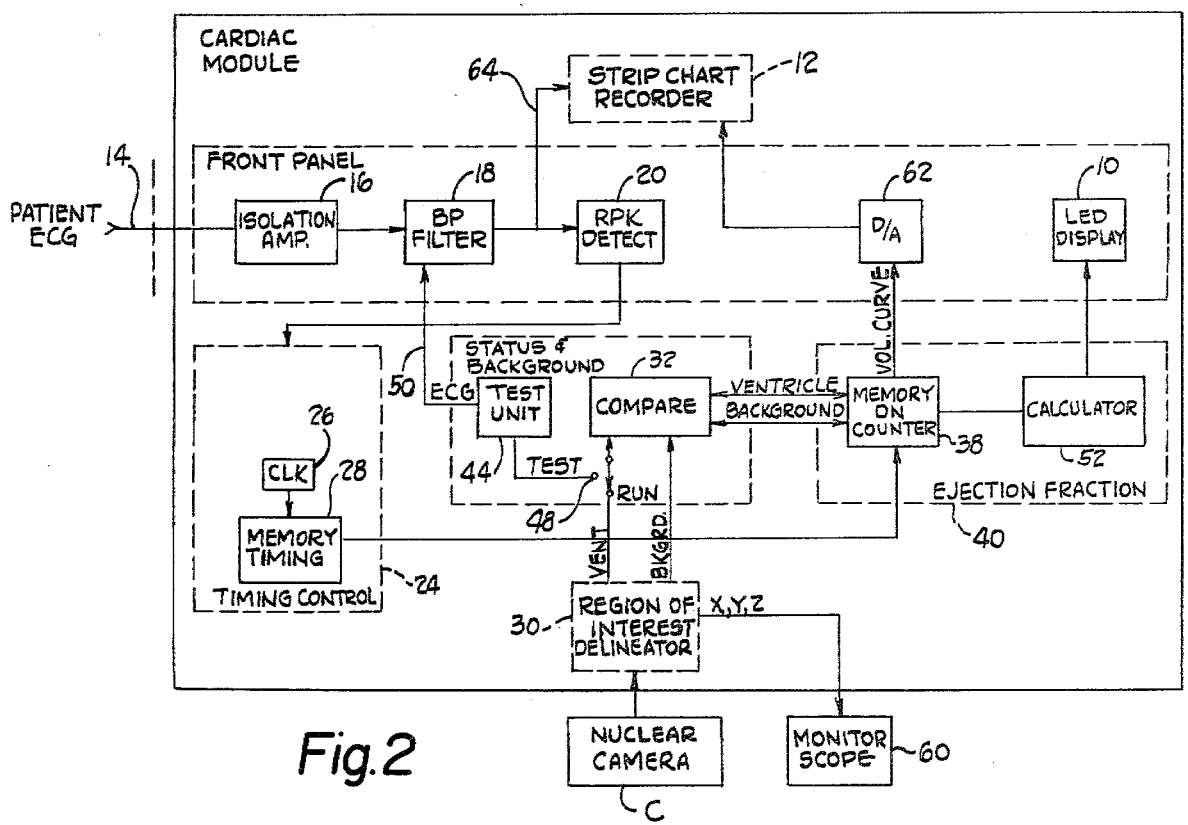
FIG. 2 is a generalized block diagram of the present invention illustrated as a portion of FIG. 1.

FIG. 2 is an overall block diagram of the cardiac module M. The electrocardiogram signal from the patient enters the cardiac module over a lead 14. An isolation amplifier 16 receives the electrocardiogram signal. The signal passes through filtering circuitry 18 and the "R" point (R-peak) of each heartbeat cycle (FIG. 1A) is detected by an R-peak detector circuit 20. This detected series of R-peaks are used to synchronize the system M with the occurrence of each such peak for proper gated ejection fraction calculations.

Timing control circuitry for the cardiac module is illustrated within the dotted box indicated 24 in FIG. 2. The timing control circuitry produces timing pulses required by other components of the cardiac module to enable its operation. The timing control circuitry consists of crystal controlled clock 26 and a set of multiple scale downcounters 28 which provide appropriately timed control pulses at various timing intervals.

A region of interest delineator 30 electrically defines a predetermined region of interest within the field of view of the camera C. The region of interest delineator 30 discriminates between data from within the left ventricle ("central" region of interest) and data from a second, or "background", region of interest, and rejects data corresponding to radiation events occurring outside either of these regions. The region of interest delineator delineates three circular areas whose combination results in the central region of interest and the background region of interest areas, respectively. The central region of interest comprises two partially overlapping circles, which together are rather similar to an ellipse. The background region of interest, in one ("first pass") mode, is defined by the area exclusive to a third circle, somewhat larger than, and concentric with, one of the other two circles. This background region of interest thus is represented by an approximately horseshoe configuration. See, e.g., the configuration illustrated in FIG. 11, the generation of which is discussed in more detail below.

The central region of interest is adjustable in size, shape and rotative attitude.

In another ("equilibrium") mode, the central region of interest is displaced separately from the central region, and does not overlap or lie adjacent to the central region.

Comparator circuitry 32 determines which of the representations of nuclear events corresponds to events taking place within the central and background regions of interest, respectively. The comparator circuitry 32, in cooperation with ejection fraction calculation circuitry 40, also subtracts the radiation counts, (during each subinterval of the patient's heartbeat) which occurred in the background region, from those which occurred in the central, or ventricle-defining region. Subtraction of the background region count from the central region count, in each subinterval, is done in one of two ways, depending upon the mode of operation selected by the operator by appropriate positioning of a switch 36 on the module M (FIG. 1).

In a so-called "first pass" mode, radiation counts located within the background region are subtracted from those corresponding to radiation taking place within the ventricle region of interest in real time, as they occur, on a count-by-count basis. Counts corresponding to radiation events taking place in the ventricle are sent into the "up" input of an up-down memory counter 38, which is a portion of ejection fraction calculation circuitry indicated within a dotted box 40. Counts representing radiation events taking place within the background region go into the "down" output of the counter circuitry 38.

Priority circuitry associated with the memory counter 38 ensures that only one input (up or down) on the up-down counter is triggered at one time.

In the first pass mode, a quantity, or "bolus" of radioactive tracer material is injected into the patient's bloodstream. The cardiac module M is actuated to process radiation data from the patient's ventricle and surrounding background area for a period of only a few heartbeats. In practicing this mode, the attendant injects the bolus, and triggers the operation of the cardiac module M approximately when the bolus first reaches the heart, as shown on a monitor display scope of the camera C.

In a so-called "equilibrium mode" the attendant injects the radioactive tracer intra-vascularly, and then waits several minutes for the radioactive material to diffuse through the patient's body, until a substantially steady state of radiation is reached with respect to the patient's entire body.

In the equilibrium mode, background counts are sampled before a study of counts from the region of interest are begun. These stored background counts are subtracted from the central region of interest count at the beginning of each subinterval of the patient's heartbeat after the ventricular study is begun. In the equilibrium mode, the background count is thus a constant during the entire ventricular study. In this mode, the "down" input of the up-down memory counter is not used. Only central region of interest counts are applied to the up-down memory counter 38 in this mode.

A test circuit unit 44 is also provided. The test circuit can be switched on or off by way of a switch 48. When the test circuit is switched on, the isolation amplifier 16 is disconnected, and a simulated electrocardiogram signal is sent as a frequency modulated signal in place of the patient's electrocardiogram appearing on the lead 14. The simulated electrocardiogram signal passes over a lead 50 to the filtration circuitry 18, and is processed by the rest of the cardiac module M as though it were a real electrocardiogram.

Simultaneously, a voltage controlled oscillator in the test circuitry generates a train of pulses whose frequency varies in a manner analogous to the radiation count rate of a normal human left ventricle in the course of a nuclear cardiology study. In this way, approximately 95% of the electronics of the cardiac module M can be tested for proper timing and performance. The only circuits not thus tested are the isolation amplifier 16 and the region of interest delineator 30.

An ejection fraction calculator 52 is provided, cooperating with the memory (up-down) counter 38. The ejection fraction calculator consists of two 4-bit digital comparators, two 4-bit latches, and one ROM.

The memory counter is clocked once at the beginning of each heartbeat subinterval, the number of such subintervals per beat being selected by appropriate positioning of a control 56 on the front panel of the module M. During each such subinterval, data is accumulated into the up/down counter 38. Data into this up/down counter comes from the region of interest delineator 30 and is pre-screened by subtraction comparator circuitry 32. At the end of each subinterval of a heartbeat the contents of the counter are transferred into the memory of the circuitry 38, the address is advanced by one, and the contents of the new memory address are transferred into the up-down counter 38. More data is accumulated on the up/down counter for the next subinterval. At the end of the subinterval the process repeats until the next R peak occurs, at which time the address counter is forced to zero (the contents of memory address zero are transferred into the up/down counter). The study ends when the contents of one memory location overflow to 00 (i.e., reach 100). At this time, the digital comparator screens through the first 75% of the memory addresses retaining the smallest number. This smallest number is the value of the radiation counts representing radiation occurring within the central, or ventricular, region, when the heart is in systole. Via a ROM, the complement of that number is produced and displayed on the two digit LED display 10 on the front panel of the cardiac module. That number is the ejection fraction of the patient's ventricle.

A monitor oscilloscope 60 is coupled to the region of interest delineating circuitry 30 to display visually the configuration, size and location of the selected region of interest.

An output of the up/down counter memory circuitry 38 is directed to a digital-to-analog converter 62. The output from the digital-to-analog converter 62 is used to actuate the strip chart recorder 12 to produce a graphical representation of the time variation of blood volume within the heart ventricle, as indicated by the changing amount of radiation from that chamber. Simultaneously, the electrocardiogram signal is directed over a lead 64 to the strip chart recorder 12, which additionally records the patient's electrocardiogram. This feature enables an operator to easily correlate the ventricular blood volume with the synchronized electrocardiogram signal.

INPUT AND INTERFACE DETAILS

Figure 3:
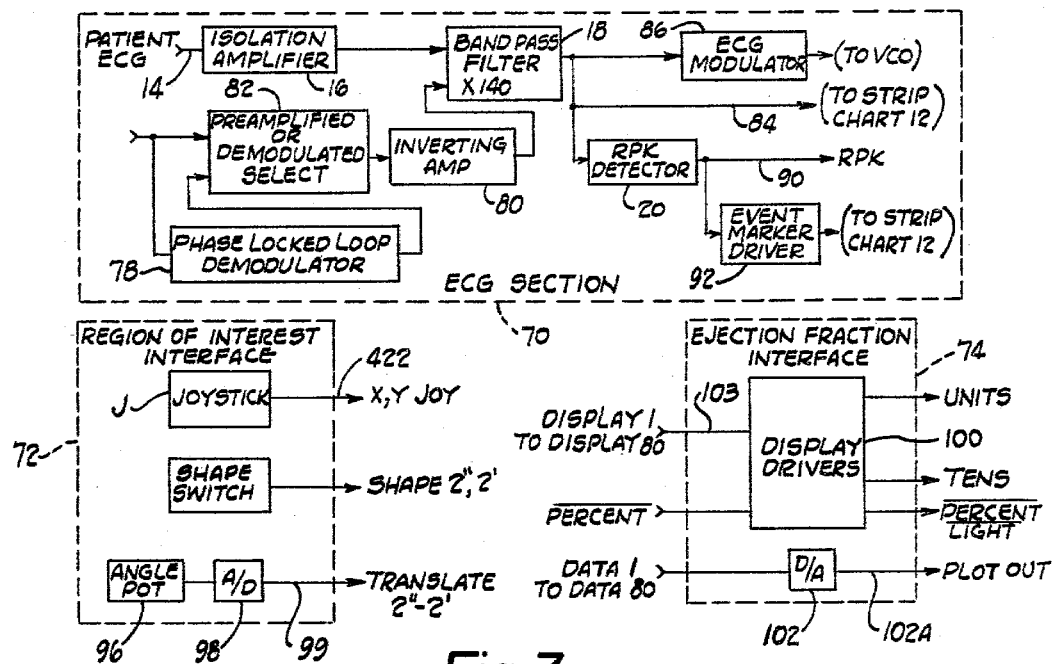
FIG. 3 is a detailed block diagram of a portion of the invention shown in FIG. 2.

FIG. 3 is a detailed block diagram illustrating input and interface components of a portion of the cardiac module circuitry described more generally in FIG. 2. FIG. 3 illustrates an electrocardiogram (ECG) section 70, a region of interest interface circuit 72 and an ejection fraction calculation interface 74.

The ECG section processes incoming ECG signals from the patient P and produces the R peak pulses. Live ECG data from a patient is presented on the lead 14 to the isolation amplifier 16, which is an optically coupled isolation amplifier having a gain of approximately 20. An input at a lead 76 can suitably be a modulated ECG signal played back from tape, a preamplified external ECG signal, or a signal from the test unit circuitry 44 (FIG. 2). If the input at the lead 76 is a prerecorded ECG signal (a modulated 4 kilohertz (khz.) signal) it goes through a phase locked loop demodulator 78 and then to an inverting amplifier 80, by way of preamp-demodulator selection circuitry 82.

Since the test signal from the circuit 44 is also a modulated 4 khz. signal, it also passes through the demodulator circuitry 78. Where the input signal on the lead 56 is an external ECG signal which is already preamplified, it goes directly into the inverting amplifier 80. The inverting amplifier 80 has a gain adjustable between 0 and 1, and is preferably set at 0.8.

Whichever of these input signals is selected passes from either the inverting amplifier 80 or the isolation amplifier 16 to the filtration circuitry 18, which is a four section band pass amplifier with a gain of approximately 140. The pass band is approximately 0.05 Hz. to 300 Hz.

This conditioned ECG signal is then fed to three downstream inputs. It passes over a lead 84, directed to the strip chart recorder 12, through a modulator 86 to be recorded, and to the R peak detector 20, the output of which is used to synchronize the operation of the cardiac module. The output of the modulator and VCO circuit 86 is transmitted to the input of a voltage controlled oscillator, with a center frequency of four khz. and a 25% deviation, to prepare the ECG signal for recording.

The R peak detector 20 comprises a 20 hz. band pass filter, an R peak threshold comparator, and a 120 millisecond (ms.) one shot. The output of the one shot synchronizes the cardiac module system timing and appears on a lead 90. An event marker driver 92 is activated each time the R peak comparator trips, marking on the strip chart recorder where in the R wave the system is synchronized.

The region of interest interface circuitry 72 provides analog to digital conversion for analog information representing the rotational position of the desired region of interest. This circuitry also provides DC reference voltages for the X-Y locations of the region of interest, and gain information.

In the ejection fraction interface circuitry 74, information describing in digital form the volume of the heart ventricle from other portions of the circuitry (discussed below) is converted to analog information by a digital-to-analog converter for printout on the strip chart recorder 12. Units and tens decoder drivers convert the ejection fraction information, expressed in binary coded decimal, to LED decimal display on the panel 10. Information describing ejection fraction percentage is sent to ejection fraction percent drivers 100 for front panel display.

Figure 3A:
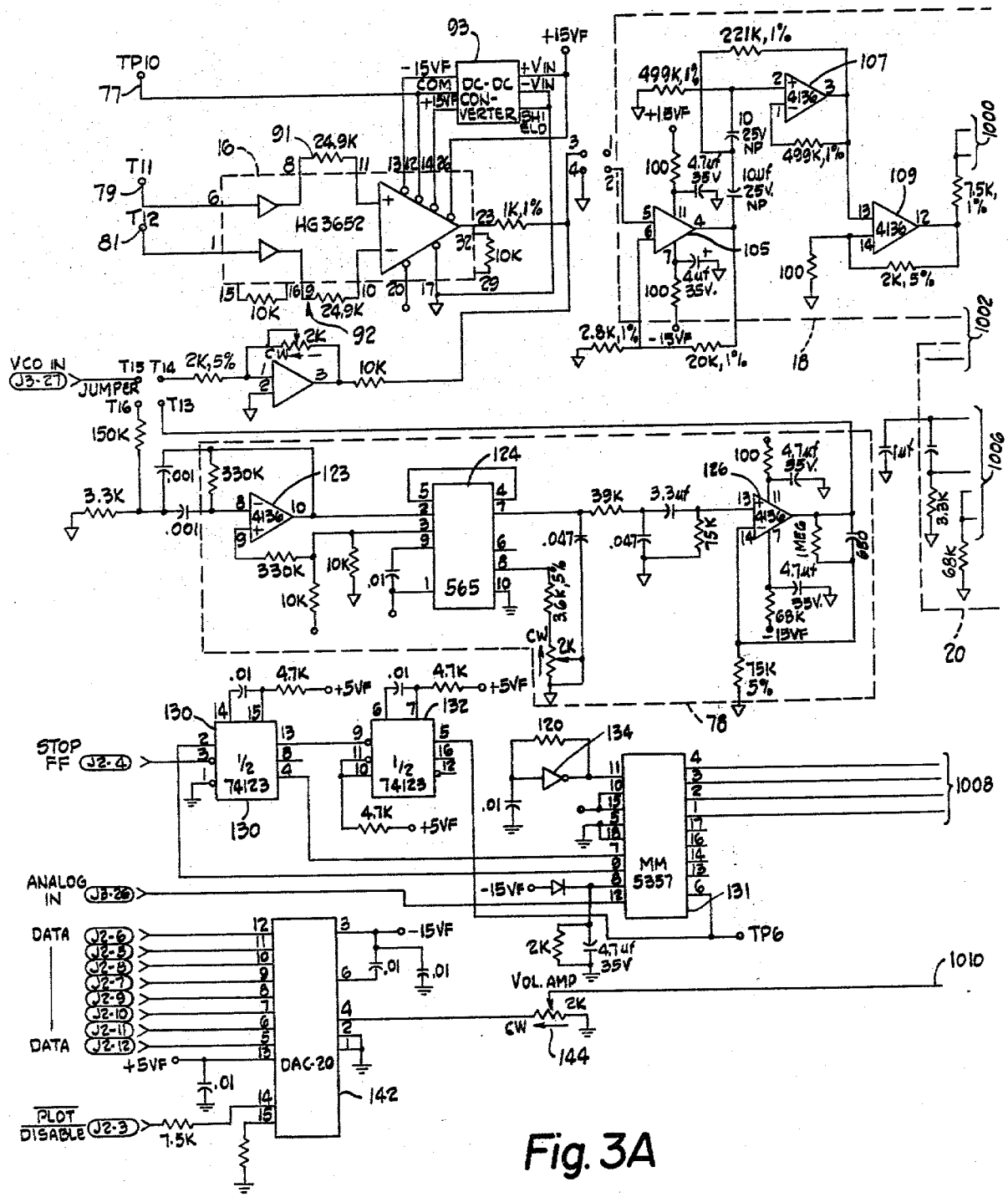
FIGS. 3A and 3B are schematic drawings of the invention portion shown in FIG. 3.
Figure 3B:
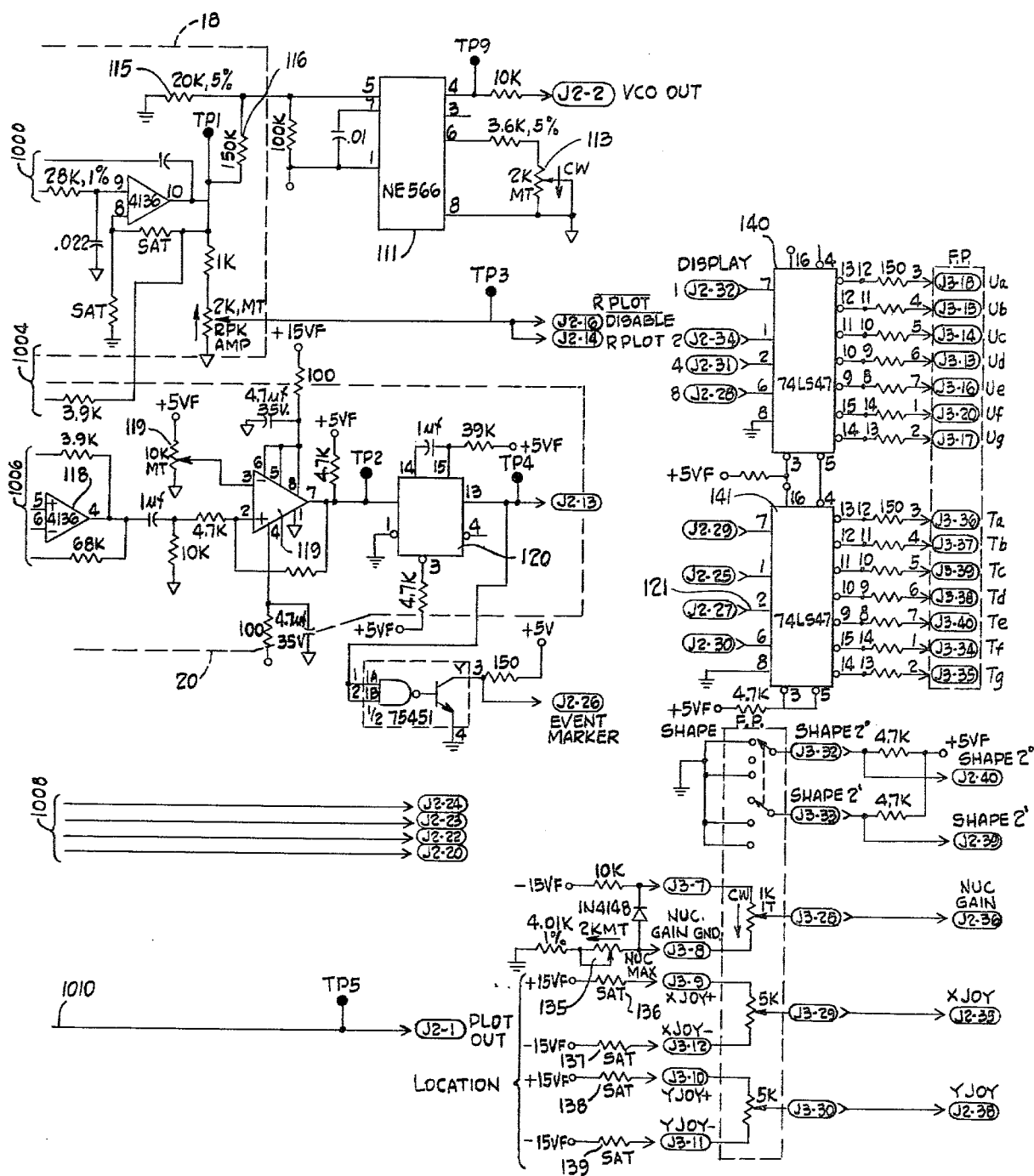

In the ECG circuitry 70, the patient's ECG signal is applied to the input 14 of the optically coupled isolation amplifier (See FIGS. 3A and 3B) at terminals 77, 79 and 81. The gain is fixed at 20. Isolated power for the amplifier 16 is provided by a high efficiency, high frequency DC to DC converter 93. The amplified patient ECG signal is adjustable. The ECG signal is then amplified 140 times by the bandpass filtration circuitry 18. The band pass filter includes a "×7" amplifier 105, a high pass filter 107 which has a low frequency cutoff of 0.05 hz., a ×20 amplifier 109 and a low pass filter 110 with a high frequency cutoff of approximately 300 hz. The output of the bandpass filter 18 is then sent to the voltage controlled oscillator 111, to the strip chart recorder 12, including provision for calibration of sensitivity of the strip chart recorder. The ECG signal is also sent to the R-peak detector 20.

The R-peak detector consists of a 20 hz. band pass filter 118, an adjustable threshold comparator 119, and a 120 millisecond one shot 120, which provides the synchronization of system timing. The R-peak detector 20 activates the strip chart recorder event marker driver 92 every R-peak, marking on the chart paper where in the heartbeat R wave, the system is synchronized.

External ECG signals (either a preamplified ECG or a frequency modulated ECG signal) can be connected to the system at the lead 76. A frequency modulated ECG signal is supplied to the phase locked loop demodulator 78. The demodulator 78 comprises an active 4 khz. band pass filter 123 with a high "Q" to attenuate all frequencies except the 4 khz. ECG signal, a phase locked loop 124 with a center frequency of 4 khz. (adjustable by variable resistance means) and an inverting amplifier 126 which has a gain of 10.

In the region of interest interface circuitry 72, (FIG. 3) analog information generated by a potentiometer 96, indicating the desired rotative position of the region of interest, is converted to digital information describing the rotation in terms of translational coordinates, by an analog-to-digital converter 98, this signal appearing at the leads 99. The conversion sequence is started by the power turn on 129 of the module, which triggers a first one shot 130 enabling the analog-to-digital converter 98 for 1.4 milliseconds. A second one-shot 132 starts the conversion process. The conversion is completed in 40 clock cycles.

The end of the conversion then retriggers the one shots 130, 132, creating a free running conversion sequence. A free running clock for the analog-to-digital converter, of approximately 600 khz., is generated by an inverter 134 connected as an oscillator. Reference voltage for the region of interest nuclear gain information is provided by variable resistance circuitry. The references provided for the X and Y locations of the region of interest are plus or minus 15 volts.

In the ejection fraction interface circuitry 74, binary coded decimal (BCD) digital ejection fraction information appearing at a lead 103 is converted to an LED display by decoder drivers 100. BCD digital volume information is converted to an analog signal for chart recorder display by the digital-to-analog converter 102, which is an eight bit D/A. The output amplitude, on a lead 102A, is adjustable by variable resistance means 144.

THE TIMING CONTROL CIRCUITRY

Figure 4:
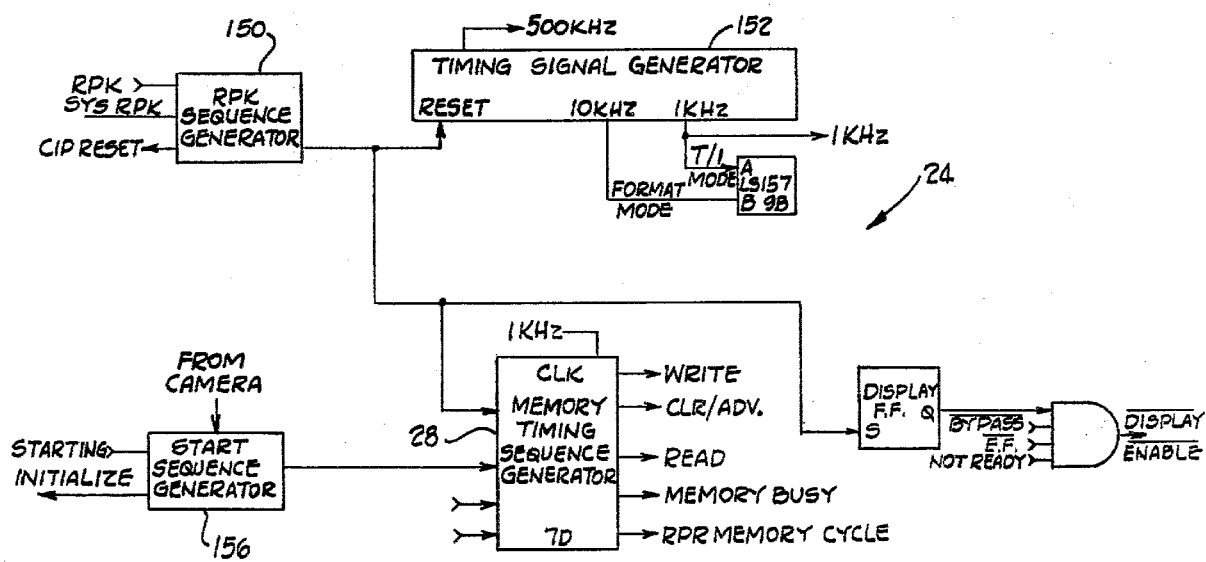
FIG. 4 is a detailed block diagram of another portion of the invention of FIG. 2.

FIG. 4 is a more detailed block diagram of the timing control circuitry 24 as illustrated in FIG. 2. The timing control circuitry includes an R peak sequence generator 150, a timing signal generator 152 and the memory timing circuitry 28.

The R peak sequence generator 150 synchronizes all the other sections of the cardiac module via four sequential signals produced by the R peak detector. The timing signal generator develops all the clock frequencies used by the system. It consists of a 1 megahertz crystal oscillator and a series of counters. The 1 megahertz oscillator is converted to a 500 kilohertz output signal for the basic system timing. The first major output of the timing signal generator 152 is a two microsecond pulse at a 10 kilohertz frequency. This is in turn converted to a 1 kilohertz frequency and serves as the clock for the memory timing generator circuitry 28.

A start sequence generator 156 is provided. Upon an impulse from a start button on the radiation camera C used in connection with the cardiac module, this sends out a pulse to initialize the memory section 28.

The memory timing generator circuitry receives a "time per channel" signal, delineating the duration of hearbeat subintervals, from a switch 160 on the front panel of the module M and produces a timing sequence equal to 1 millisecond times the front panel setting. This same sequence is also produced in response to an R-peak, with the addition of an R peak memory cycle output to indicate to the memory where R peaks occur.

Figure 4A:
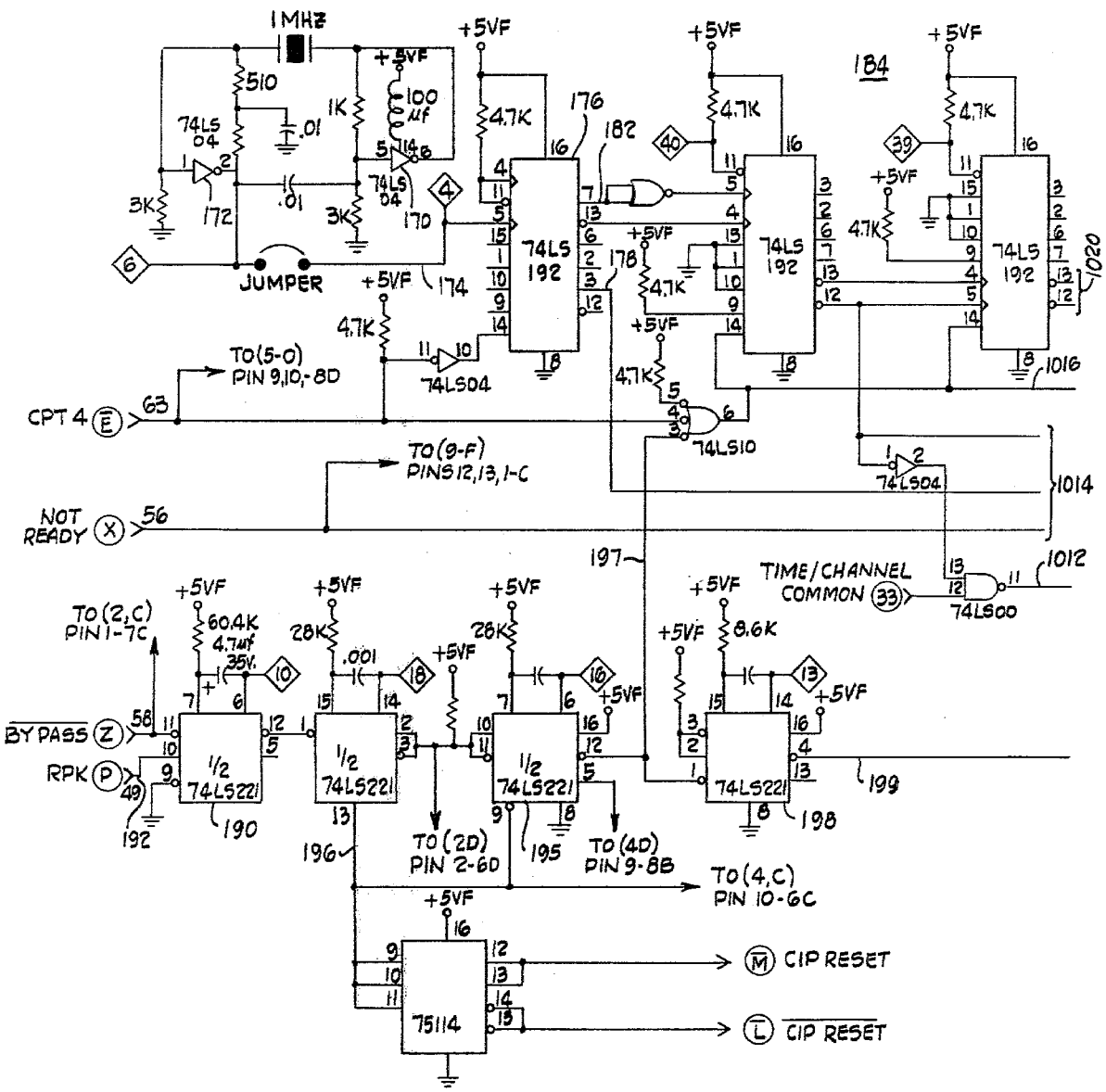
FIGS. 4A and 4B are schematic drawings of the portion shown in FIG. 4.
Figure 4B:
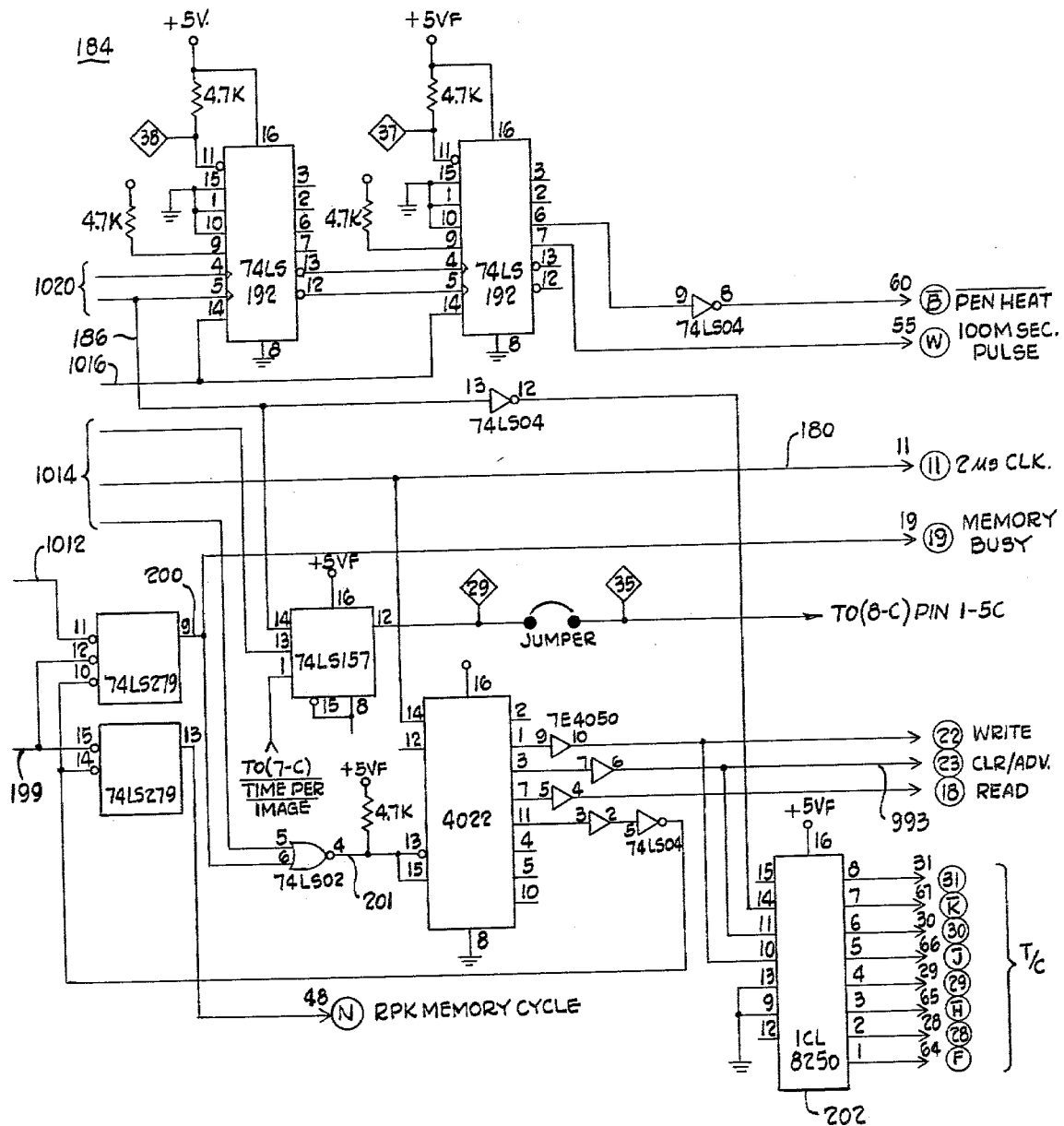

FIGS. 4A–4B illustrates the timing circuitry 24 in schematic form. The timing signal generator 152 includes a 1 megahertz oscillator. This oscillator comprises a 1.008 megahertz crystal and two sections 170, 172 of amplifier circuitry, and associated circuitry. The 1 megahertz output signal is fed by way of a lead 174 into another solid state divider circuit component 176. An output lead 178 of the divider circuitry 176 produces a 500 kilohertz signal which is used to time the memory timing sequence generator 28. This output is also directed (as a 2 microsecond clock pulse train) to the ejection fraction calculation circuitry to produce memory timing signals in a manner described below, over a lead 180. The output appearing on a lead 182 (100 kilohertz) is inverted and used to drive a chain of circuitry generally indicated at 184. A 1 kilohertz output appearing on a lead 186 is employed in generating timing pulses to divide each heartbeat cycle into the predetermined number of subintervals.

A series of one shots synchronizes the system with the R peak signal. A one shot 190 acts as a pulse stretcher to prevent the system from seeing a double R peak pulse. The R peak pulses are delivered over a lead 192. A one shot 194 produces over a lead 196 a 20 microsecond pulse. A one shot 195 resets circuitry 184 over a lead 197, to assure that counts left over at the end of a cycle do not go into the first time block of the next cycle. A one shot 198 initiates each R peak memory cycle over a lead 199.

Memory timing is controlled by the outputs from the memory timing circuitry 28. When the signal on a lead 200 goes high, the signal on the lead 201 goes low, enabling the circuitry 28 to produce a series of four pulses. A signal on a lead 200 is also fed out of this portion of the circuitry to the ejection fraction calculation circuitry to prevent the counting of input pulses during memory transfers, in a manner described below.

The signal at the lead 200 is set high by either an R peak signal or a so-called "time/channel" signal indicating the beginning of a new subinterval. The signals delineating the various subintervals are generated by circuitry 202. The circuitry 202 is a two decade counter with open collector outputs. Thumb wheels wire-AND the outputs together so the signal at a lead 203 goes high when the count produced by the counter 202 equals the number set on the thumb wheels. The state of the signal at a lead 204 indicates to the memory circuitry 28 when an R peak event takes place in the patient's heartbeat cycle.

THE EJECTION FRACTION CIRCUITRY 40

Figure 5:
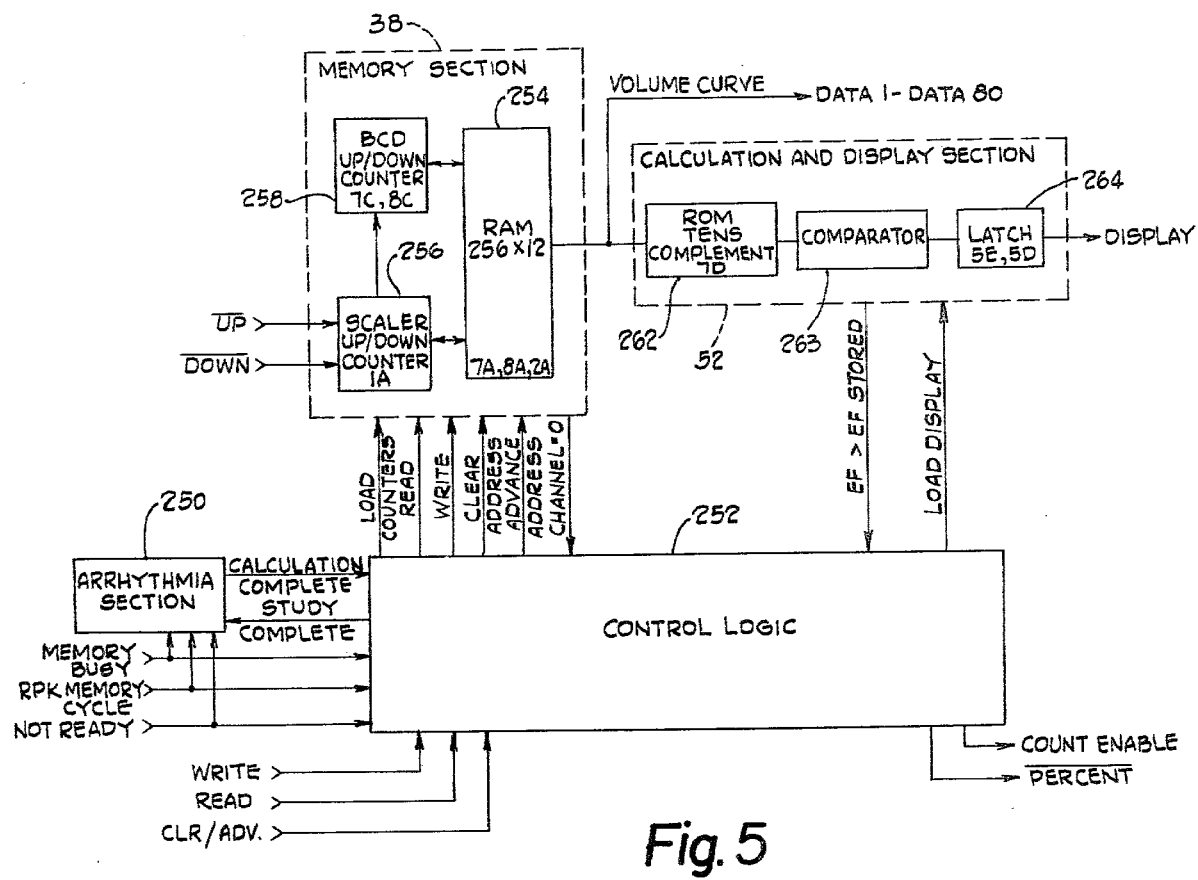
FIG. 5 is a detailed block diagram of another portion of FIG. 2.

The ejection fraction circuitry 40 is shown in detailed block form in FIG. 5. The ejection fraction circuitry 40 contains the circuitry which accumulates gated data into a multichannel memory and calculates and displays the ejection fraction at the end of each study. It includes the memory section 38, the calculation and display section 52, an arrhythmia control section 250 and a control logic section 252.

The memory section 38 comprises three random access memories (RAM's). The RAM's are each 256×4, set-to provide 256×12 memory, three bidirectional bus drivers, three up/down counters and associated logic. Each memory channel has eight bits for main storage of two binary coded decimal (BCD) digits, and four bits for scalar data. Incoming data to the memory 38 is first divided by a scaling factor loaded into the binary up/down counter 256. The results of this scaledown are fed to the BCD up/down counters 258 and stored into the memory. Communication between the memory 254 and the up/down counters occurs with every subinterval (time/channel) signal via the bidirectional bus drivers. When a subinterval defining signal occurs, the number accumulated in the up/down counters is transferred into a channel of the memory 254. The remainder of counts left in the binary scaler counter 256 is saved as binary (not BCD) data.

Next, the memory address of the memory 254 is advanced to the next channel, and the contents of that next channel are transferred into the up/down counters 256, 258. The signals commanding the information transfer and memory channel advances are short pulses generated in the timing control circuitry indicating the subinterval definition.

More data is accumulated into the up/down counters 256, 258 during the next defined subinterval. When the next subinterval defining signal occurs, the sequence described above is repeated and the contents of the next memory address channel are similarly updated.

When an R peak signal occurs, the memory address is cleared to zero and the contents of the zero memory channel are transferred to the up/down counters 256, 258.

The calculation and display section controls the LED display 10 on the front panel and determines the ejection fraction. During the study, the LED display displays the contents of the zero channel of the memory 254. The study terminates when one of the memory channels accumulates a count of 100. At that time, the calculation and display section 52 searches approximately the first ¾ of the memory channels for the smallest number stored, and displays the complement of that number on the LED display, together with a "%" sign.

To execute the memory search, the contents of each memory channel of the memory 254 are fed to the address leads of a read only memory (ROM) 262. The contents of the ROM 262 at that address is the tens complement of the address (e.g., 100 minus the address). For example, if the memory channel contains an accumulation of "03" at address channel No. 3 of the ROM is stored 100 minus 3, or "97".

The output of the ROM 262 is compared with the preceding outputs of the ROM, generated in connection with the other address channels, and each time a larger number is encountered it is stored into a latch circuit 262 by way of a comparator 263. At the end of the memory search, the number in the latch 264 is displayed as the ejection fraction.

The largest number accumulated in any single one of the address channels of the memory 254 represents the diastolic volume of the left ventricle. This is by definition always 100, because counting in the study stops when the first of the memory channels accumulates a count of 100. Therefore, substituting 100 for the diastolic volume, the ejection fraction in percent equals 100 minus systolic and all that is (1) over 100 and (2) times 100.

Cancelling out the 100 from the numerator and denominator, the ejection fraction in percent equals 100 minus the systolic volume.

At systole, the volume of blood in the left ventricle is at its lowest. The systolic volume is the smallest number stored in the memory. Thus, the ejection fraction is the tens complement of the smallest number accumulated into any of the channels of the memory 254 during the study, i.e., 100 minus that number.

The arrhythmia section 250 compensates for normal variations in heart rate during a study. It tells the calculation and display circuitry 52 how many channels of the memory 254 to use in determining the ejection fraction. Usually, a typical patient has some amount of arrhythmia (i.e., variable heartbeat rate). Some heartbeats last long enough to put data into the last used memory channel of the memory 254. Some heartbeats, on the other hand, end before the last channels are reached. This causes the last used channels of the memory to end up with spurious data. Therefore, in the preferred embodiment, the last 25% of the memory channels used in the study are ignored when the ejection fraction is determined.

This is accomplished by screening the memory for only ¾ of a heartbeat cycle, as defined by the time interval between adjacent R peaks. If, for this purpose, one R peak interval is selected at random, it may be too short (not enough channels will be used to determine the ejection fraction with desired accuracy) or too long (channels with erroneous data will be used in computing the fraction).

To avoid this difficulty, the R peak interval used to determine the memory screening time is the average of the first sixteen R peak intervals.

Figure 7:
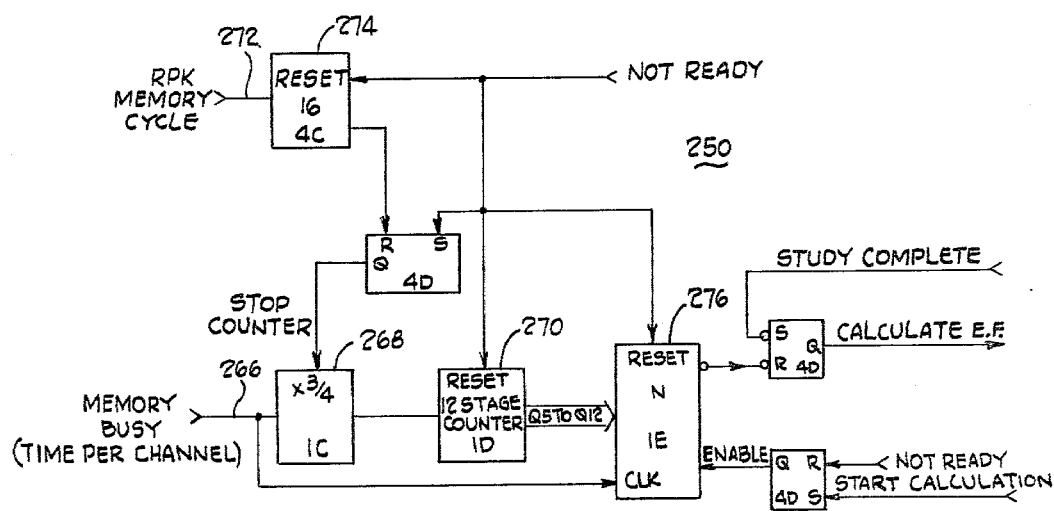
FIG. 7 is a detailed block diagram illustrating a portion of the invention shown in FIG. 2.

The arrhythmia section 250 is illustrated in more detailed block form in FIG. 7. The ¾ R peak which is based on an average of 16 R peak intervals is determined and stored at the beginning of the study. "Memory busy" pulses, each initiated by a subinterval definition pulse and appearing on a lead 266, are multiplied by ¾ in a multiplier circuit 268, and stored into a 12 stage counter 270 for the duration of 16 R peak pulses. The R peak pulses are fed over a lead 272 to a divide by 16 counter 274. When 16 R peak pulses have been detected, the counting of the pulses on the lead 266 is stopped.

At that time, the number represented in storage in the counter 270 represents ¾ of the subinterval defining pulses which occurred during the 16 R peak intervals. If the first four storage stages of that counter are ignored, the remaining number in the counter 270 represents 1/16 of the original stored number. This number (contained in stages 5 to 12 of the counter 270) is used to preset another counter 276.

At the end of the study, the pulses on the lead 266 have stepped down the counter 276 from the preset value to zero. This time period represents the ¾ of average R peak interval used for memory screening by the calculation and display section 52.

The control logic section 252 provides control pulses for the other sections of the ejection fraction circuitry to perform their functions. It generates the pulse sequence that determines communication between the up/down counters 256, 258 and the memory 254. It also creates pulses which initiate and stop the data accumulation, and controls the display of the "%" sign.

Figure 6A:
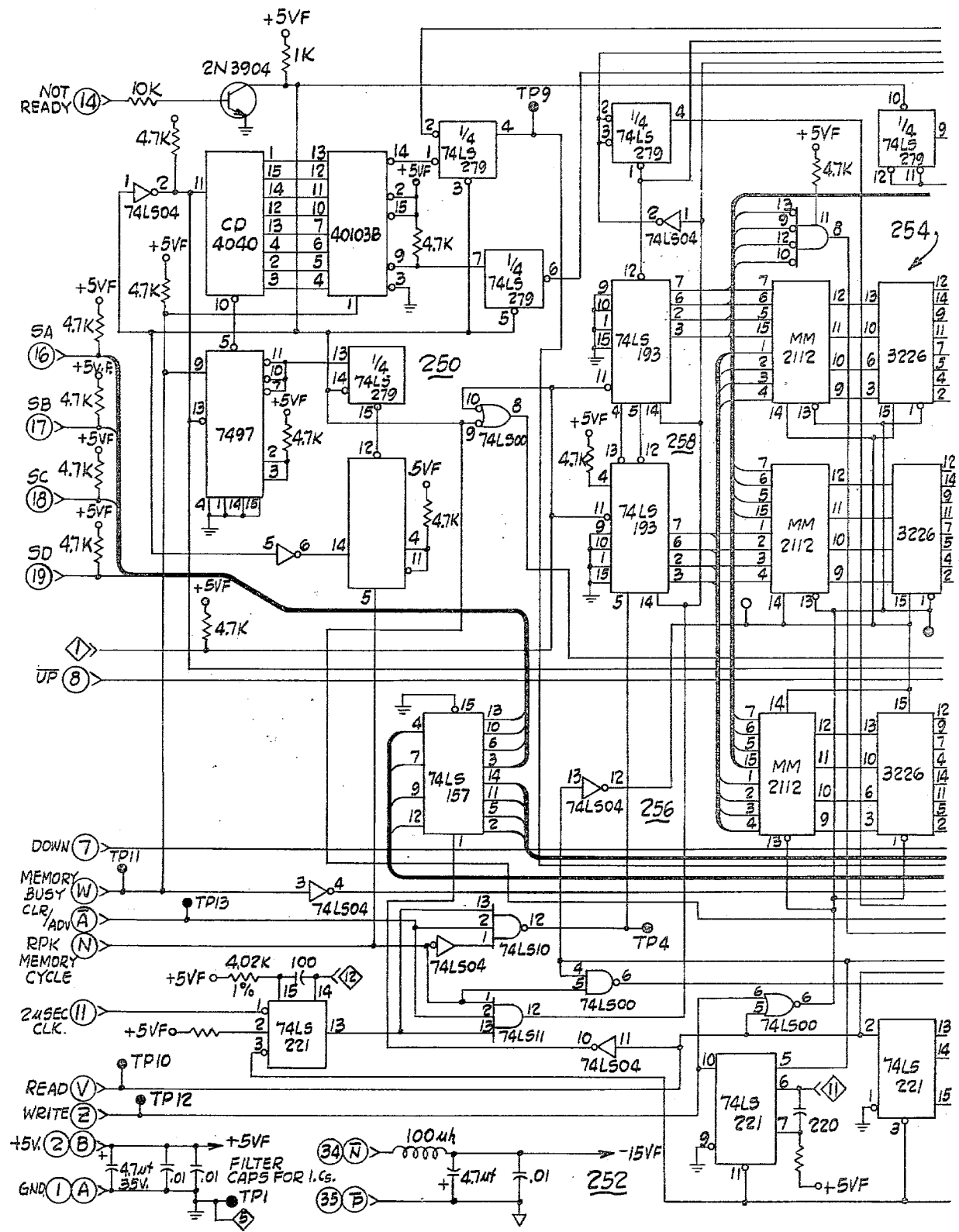
FIGS. 6A and 6B are schematic drawings of the portion shown in FIG. 5.
Figure 6B:
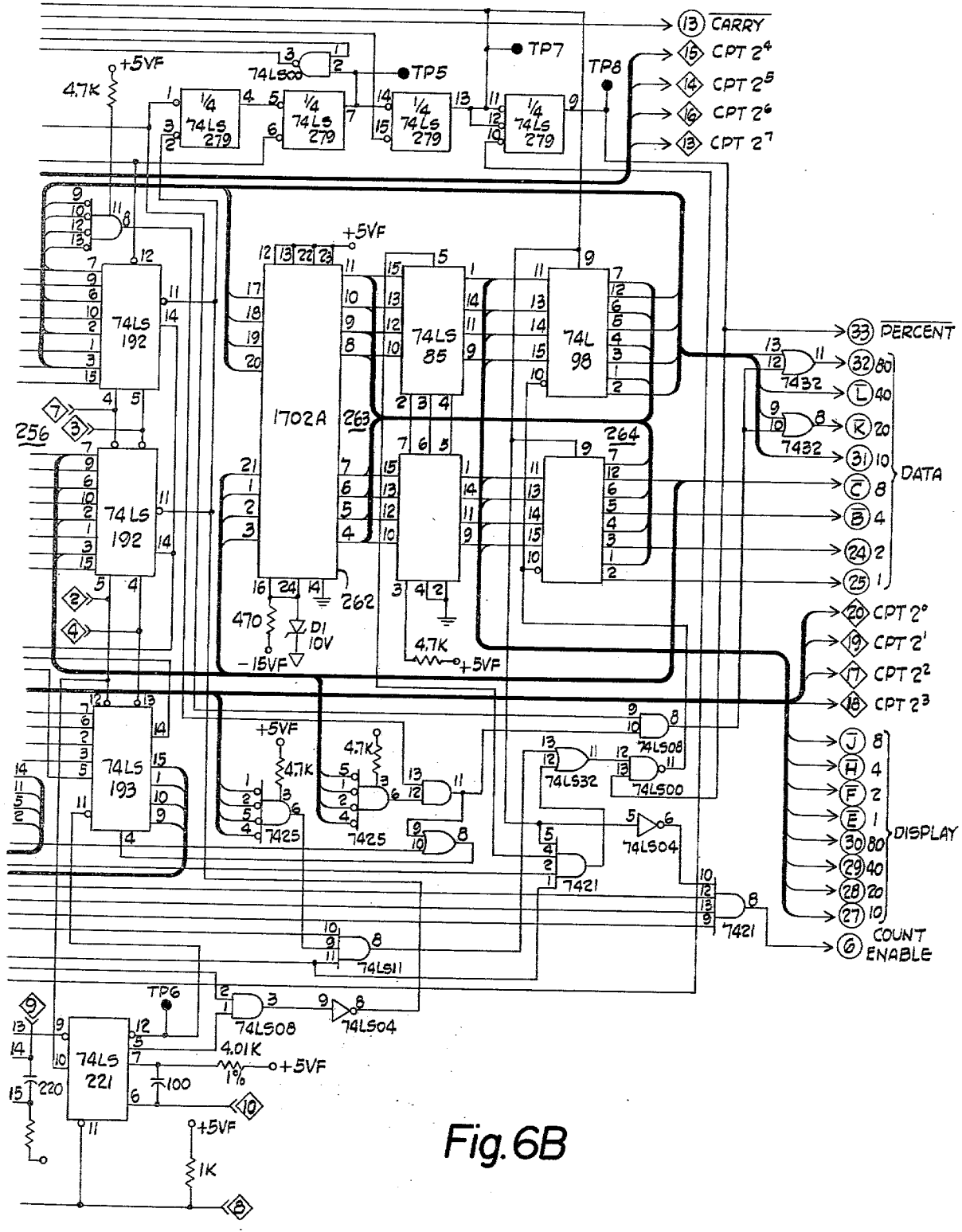
Figure 8:
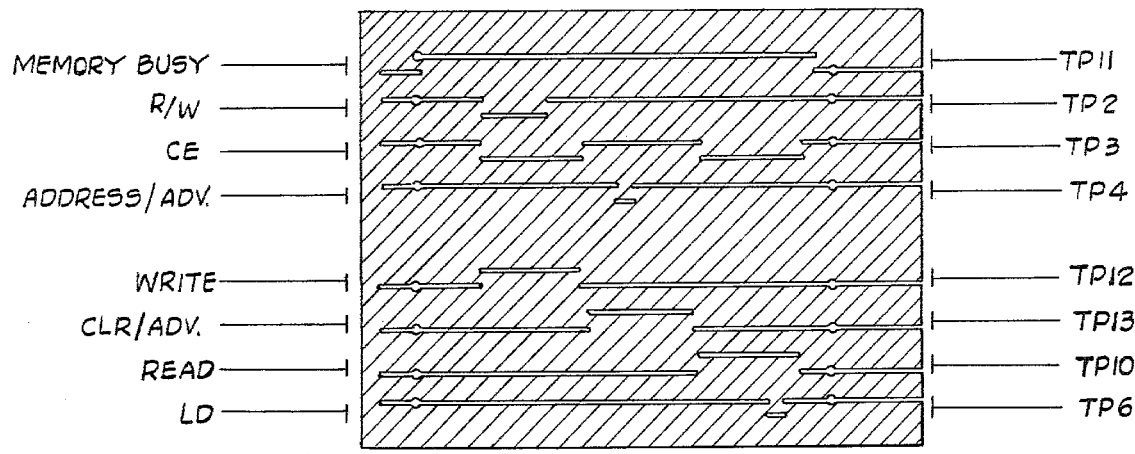
FIG. 8 is a timing diagram illustrating operation of a portion of the part of the system shown in FIG. 5.

FIGS. 6A and 6B are schematic diagrams encompassing the circuitry illustrated in block form in FIGS. 5 and 7. FIG. 8 is a timing diagram illustrating the timing sequence of several of the signals correspondingly indicated in FIGS. 5 and 7, and will be helpful with respect to understanding the detailed operation of the ejection fraction circuitry.

One shot circuits 300, 302, 303, 304 provide timing pulses for a memory system. These pulses are illustrated in FIG. 8, as indicated above.

The "write", "clear/advance" and "read" signals are timing signals produced by the main timing control circuitry 24. The one shots 300, 302, 303, 304 produce the "R/W", "address advance" and "load" signals properly related to circuitry 305, and circuitry 306 ensures that data is stored and read while it is stable.

Counting circuitry 308, 310 comprise an 8 bit binary counter which generates the address control signals for the 256×4 memory 254, consisting of circuit chips 312, 314, 316. Circuitry 318, 320, 322 are bidirectional bus drivers which control the direction of data flow to and from the memory 254.

324, 326, are decade counters which are used both as a work register for the memory 254 and as an information register for the digital volume curve defining information sent over a set of leads 330 to the digital-to-analog converter 102 (FIG. 3). Circuitry 332 is a four bit binary counter used as a counter for dividing by the number of memory channels. On a "read" cycle, the "select" line at circuitry 335 goes low, so that memory inputs from the memory 254 are passed and loaded into the counter 332. The counter 332 then counts the input pulses up or down, as appropriate. If the signal of the lead 336 goes low, the counter "load" lead 338 is driven low by the signal appearing at the lead 340 on the one shot circuit 304. At this time the left-hand outputs of the circuit 335 come from the inputs on the pins 13, 10, 6, 3. These inputs represent the "ones" complement of the selected address number, and in another set of pulses another output signal will appear on the lead 336 of the circuitry 332.

If a "write" pulse occurs, the current value stored in the counter 332 is stored in the memory circuitry 316, so that the remainder stored in the counter 332 is remembered from one R peak to the next. A chain of flip-flops, generally indicated at 350, controls the functions of the ejection fraction calculation circuitry. When a "not ready" pulse is produced, it ripples through this chain of flip-flops, resetting the first two flip-flops and setting the third. The signal at the lead 352 goes high in response to the accumulated contents of one of the channels of the memory 254 reaching a value of 100. This enables a signal at the lead 354 so that, at the end of a current R peak interval, the counter inputs will be disabled, i.e., the "count enable" lead goes low. The signal at the lead 354 also enables a flip-flop 356 (in the arrhythmia seciton). When the signal at the lead 354 goes high (indicating that the study is complete) the cardiac module M begins to calculate the ejection fraction. The calculation takes place during a length of time determined by the arrhythmia section 250. When the signal at the lead 358 goes low, the calculation is cut off and the front panel "%" sign is actuated to display that sign.

The ejection fraction calculation section 52 includes the ROM 262, the comparator circuitry 263, including circuits 361, 363, and the latching circuitry 264, including circuitry 365, 367. During the study, the latching circuitry 365, 367 output at the leads 368, 370 are low, selecting all the right-hand leads on the circuitry 365, 367, with the exception of pin 7. This information is clocked in when the unit is selecting the zero memory channel, and a "write" pulse occurs. Thus the contents of memory channel zero are displayed on the front panel 10 and updated at the occurrence of each R peak signal, giving an approximate percent of the study which is completed.

When the signal at the lead 354 goes high, indicating the study is completed, the latching circuitry signals at the leads 368, 370 go high, selecting the right-hand inputs of those chips, with the exception of the leads at pin 2. These are the outputs from the ROM 262.

The ROM output, as explained above, equals 100 minus its input for inputs greater than 15. For inputs less than 15, its output is zero F (hexadecimal). The ROM output is latched into circuitry 361, 365 when the zero address channel is interrogated and a "write" pulse occurs, to act as an initial reference.

Since the zero channel is interrogated at each R peak event, this channel should be near 100. The unit then compares each against this channel, until the signal at the lead 370 goes high, indicating that the ROM output is greater than the number previously stored. At such a time the latching circuitry 365, 367 latch the current output of the ROM and continue the comparison. At the end of the calculation the latching circuitry 365, 367 holds the ROM's largest output achieved during the information scanning cycle.

The arrhythmia circuit 250 prevents a calculation section from using invalid channels, i.e., possibly bearing spurious information, for its calculation. When a "not ready" pulse occurs circuitry 372, 374, 376, 378 and 380 are all reset to their initial states. Circuitry 374 is a binary rate multiplier. Its output equals its input times 0.75. Its output pulses are counted by the counter 372. The counter 376 counts the R peak memory signals. When the 16th R signal occurs, the signal at the lead 382 goes low. This sets the signal at the lead 384 and the circuitry 380, disabling the counter 374. At this point the counter 372 holds ¾ of the "memory busy" or subinterval definition pulses which have occurred during the first sixteen R peak cycles. The output of the counter 372 is shifted four bits to divide by 16. Thus the input to the circuitry 378 equals ¾ of the average number of subinterval definition pulses taken over the first sixteen peak cycles. The signal at the lead 387 is held low. This continuously loads the counter 378 with the outputs of the counter 372. When the study is complete, the signal at the lead 387 goes high, enabling the counter 378. When the signal at a lead 390 goes low, it resets circuit 356 which disables the calculation clock (pin 10 of the circuits 365, 367 by way of the signal at the lead 393).

THE REGION OF INTEREST DELINEATOR 30

Figure 9:
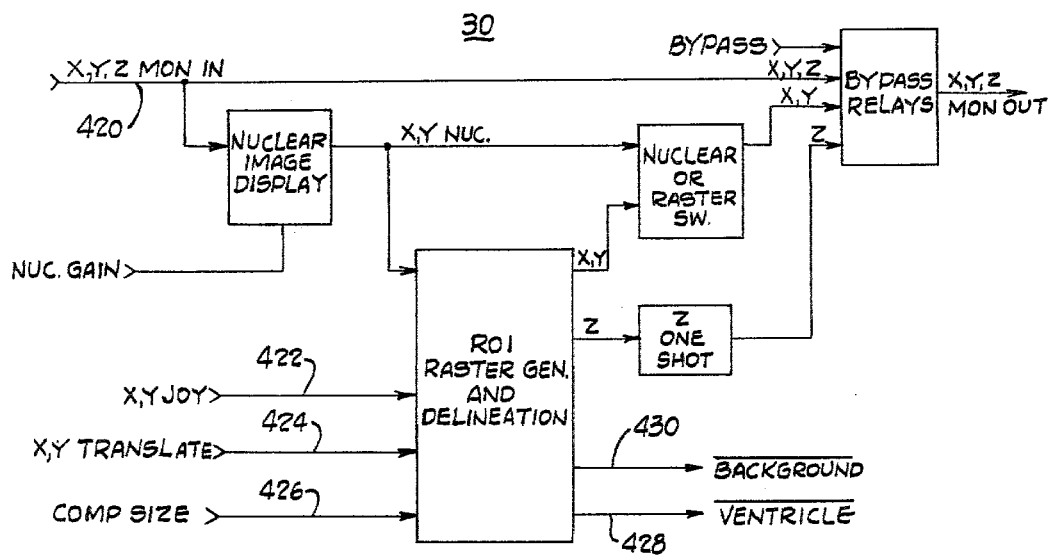
FIG. 9 is a more detailed block diagram illustrating the portion of the system shown in FIG. 2.

The region of interest determining circuitry is illustrated in detailed block form in FIG. 9. The inputs to the region of interest board are the X, Y and Z signals from the nuclear camera, indicating the two-dimensional locations and intensity of radiation events sensed by the camera C. Also input is information from a "joy stick" J (FIG. 1) on the front panel of the cardiac module M. The joy stick produces X and Y information indicating the desired location of the region of interest, as selected by appropriate positioning of the joy stick J. These signals appear on a set of leads summarily represented at 422 (See also FIG. 3). Other inputs include signals indicating X and Y translation and size information from other portions of the system, which are described below, which information appears on leads 424, 426, which are in actuality multiple leads carrying the various aspects of this information.

The region of interest circuitry 30 generates an X and Y raster, calculates the circle formulae for the circles used to represent the regions of interest, and generates Z unblank pulses to display these regions on a monitor oscilloscope. It also sends the nuclear image of radiation events to the monitor scope for display. It decodes to indicate which nuclear events occurred within the central region and the background region. Signals indicating events occurring within the central region are transmitted on a lead 428, and those corresponding to the background region are transmitted on a lead 430.

The region of interest circuitry 30 produces three sets of signals. It produces X and Y raster signals, Z unblank pulses to display circular regions of interest and Z unblank pulses to display nuclear events. It also decodes those nuclear events occurring within central and background regions of interest delineated by the circuitry 30 and produces indications of the occurrence and selective locations of these events to other circuitry of the cardiac module, as described in more detail below.

Figure 10:
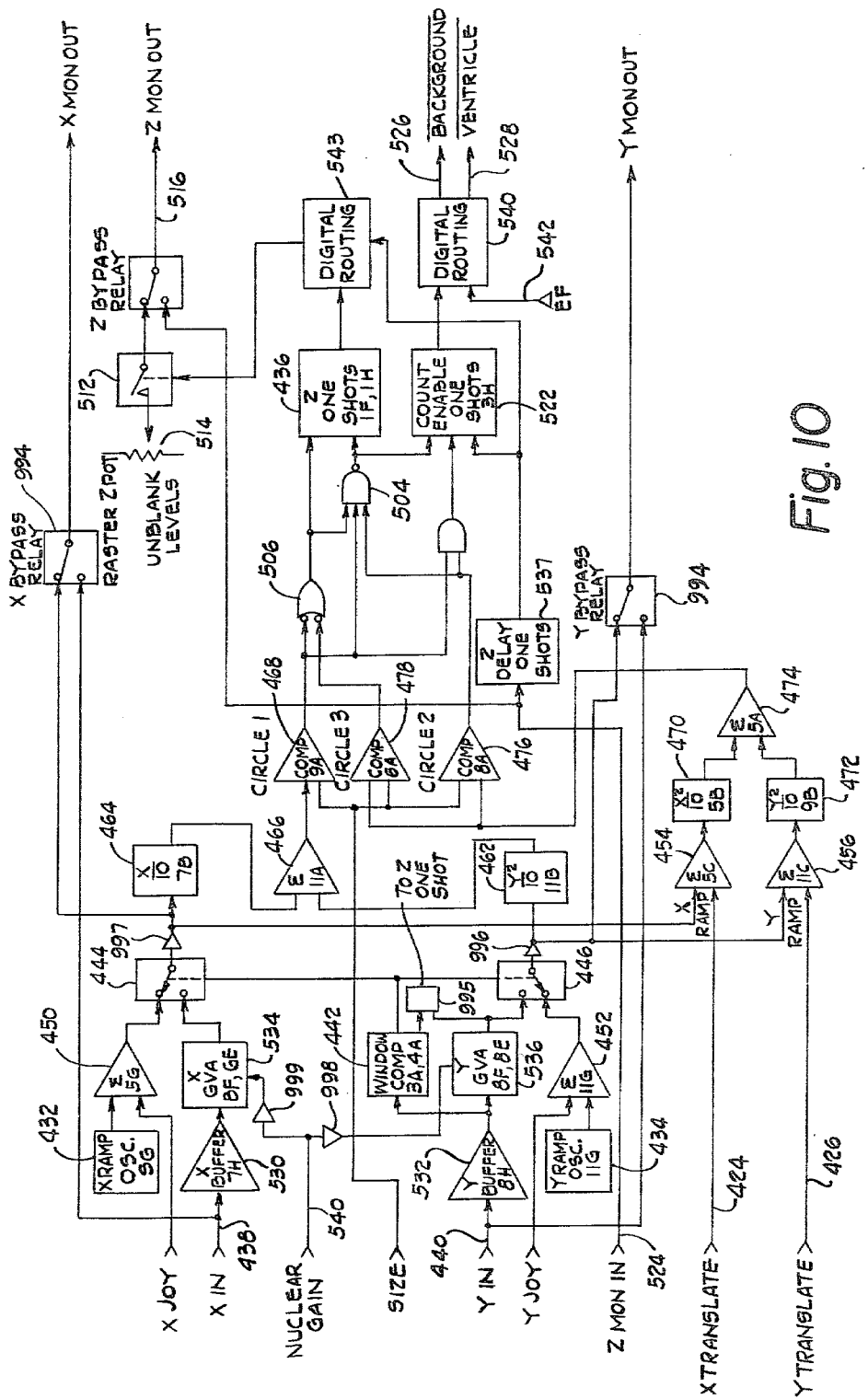
FIG. 10 is a detailed block diagram illustrating the portion of the system shown in FIG. 9.
Figure 10A:
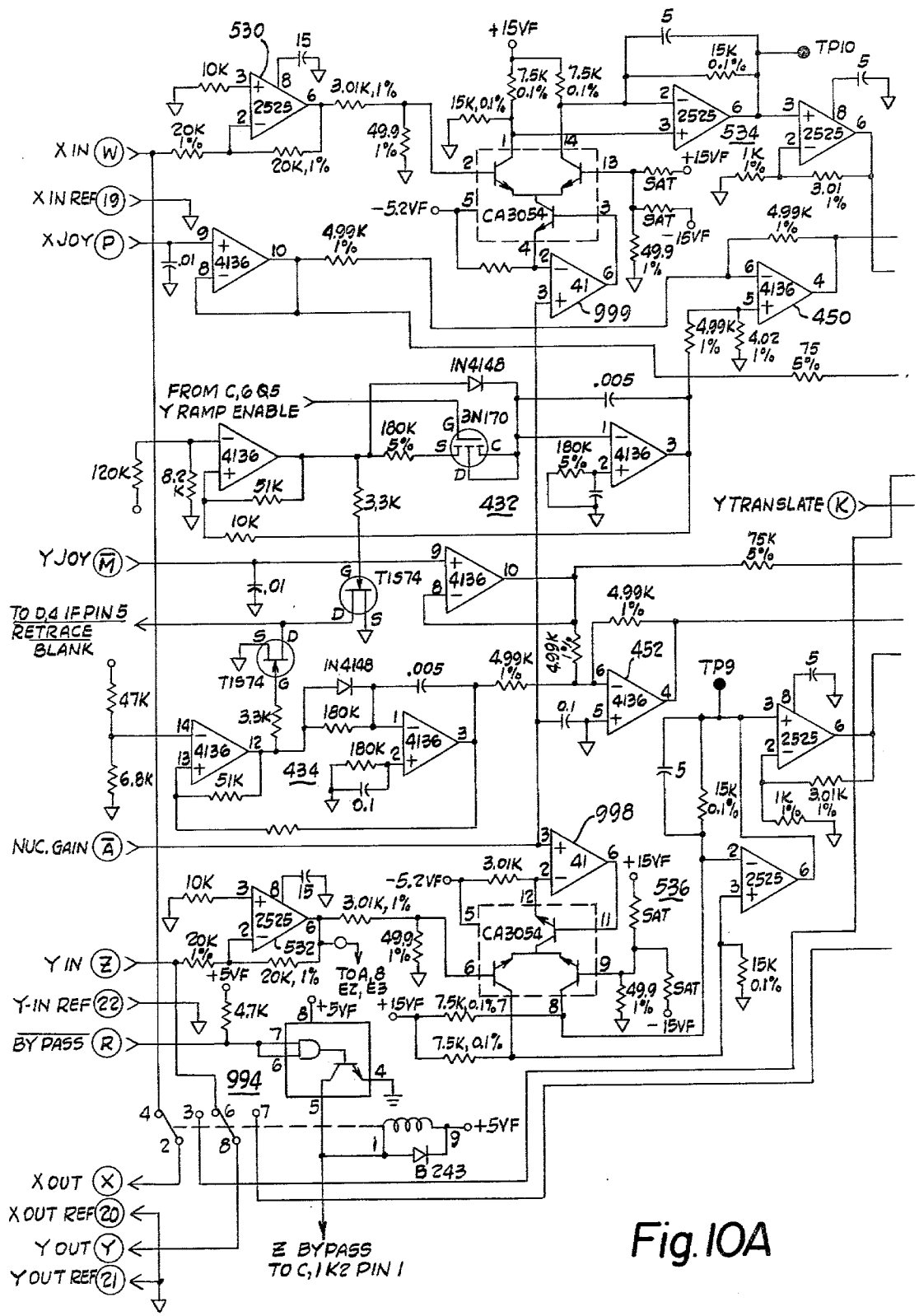
FIGS. 10A–10D are schematic drawings of the portion shown in FIG. 10.
Figure 10B:
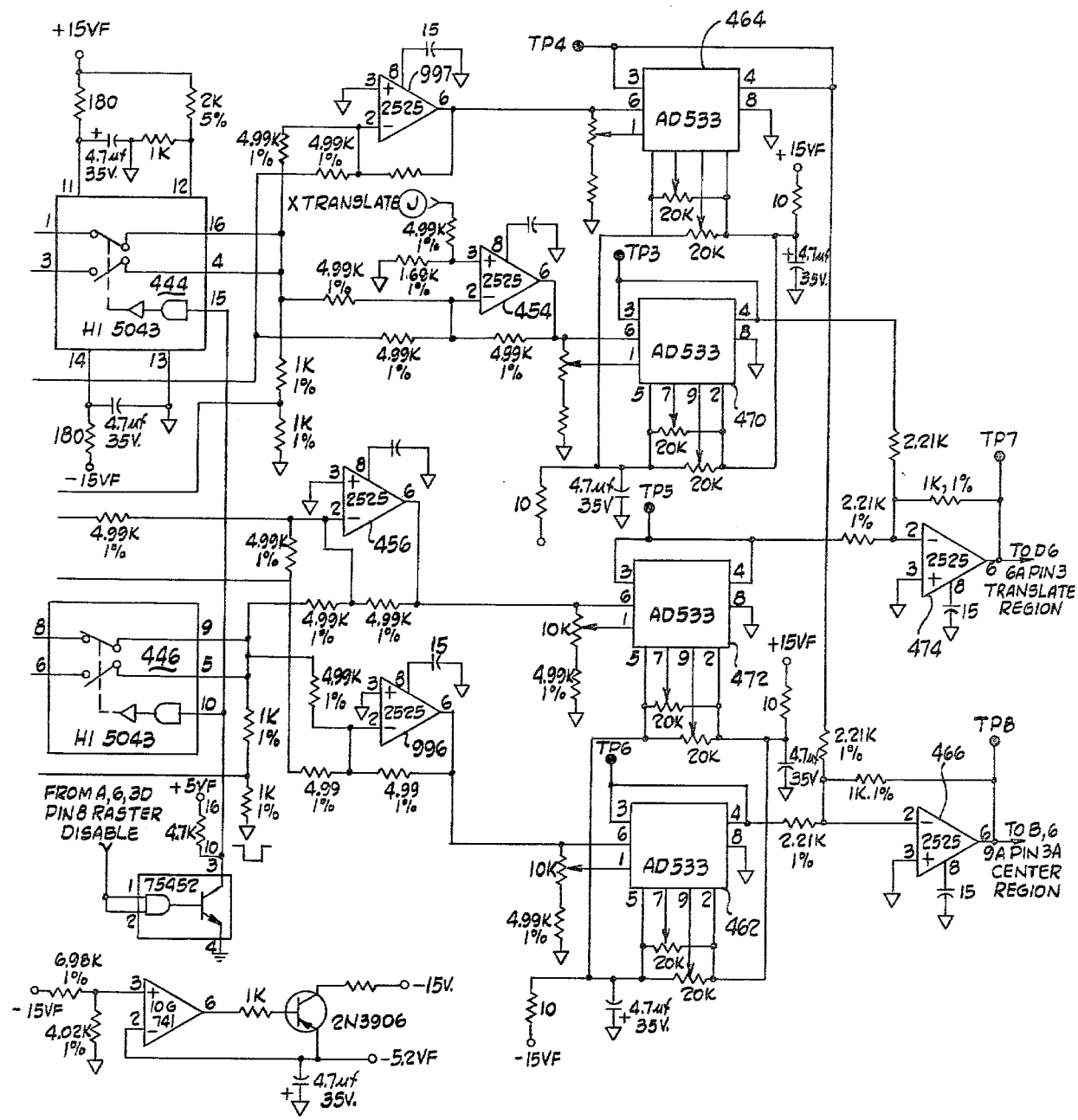
Figure 10C:
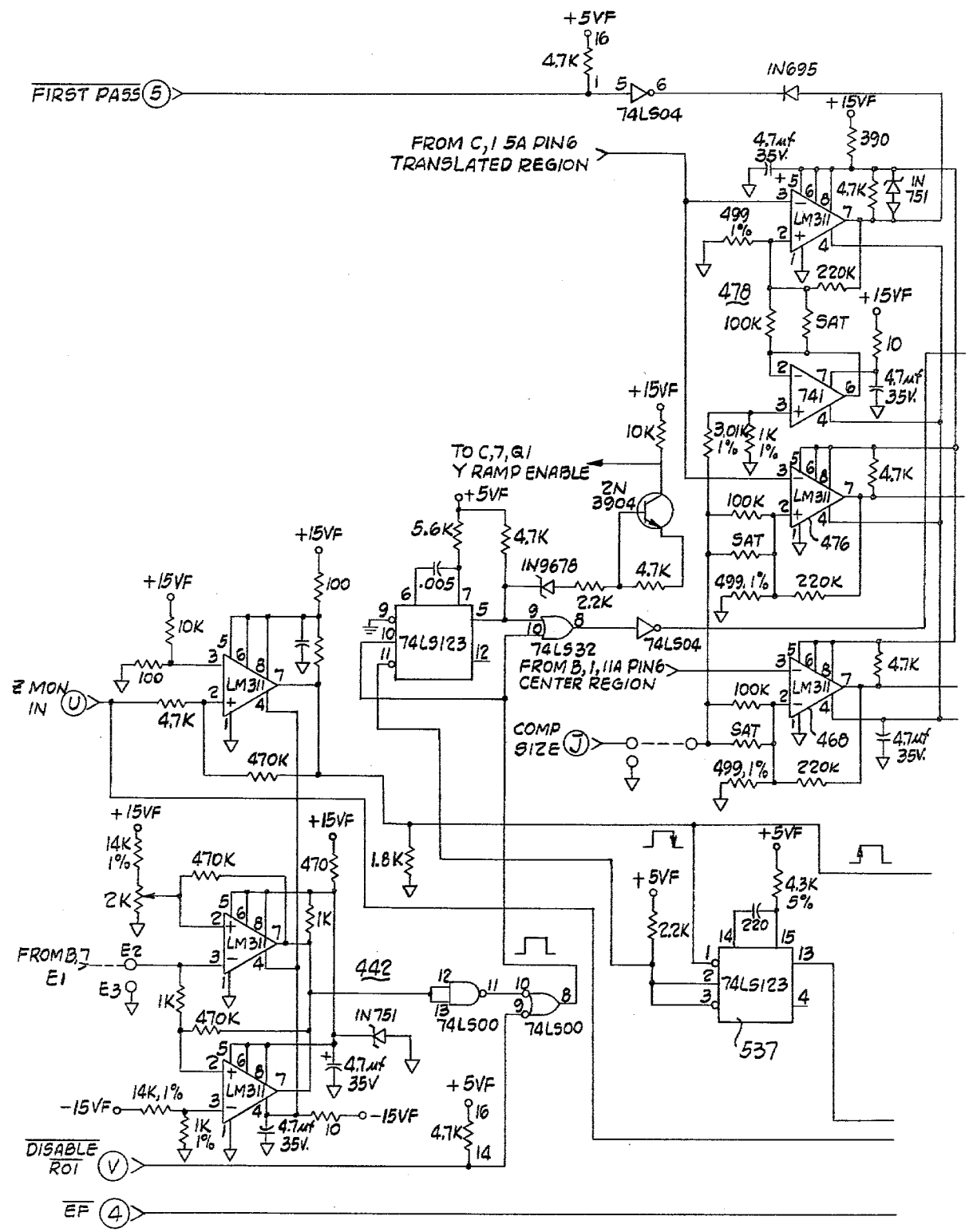
Figure 10D:
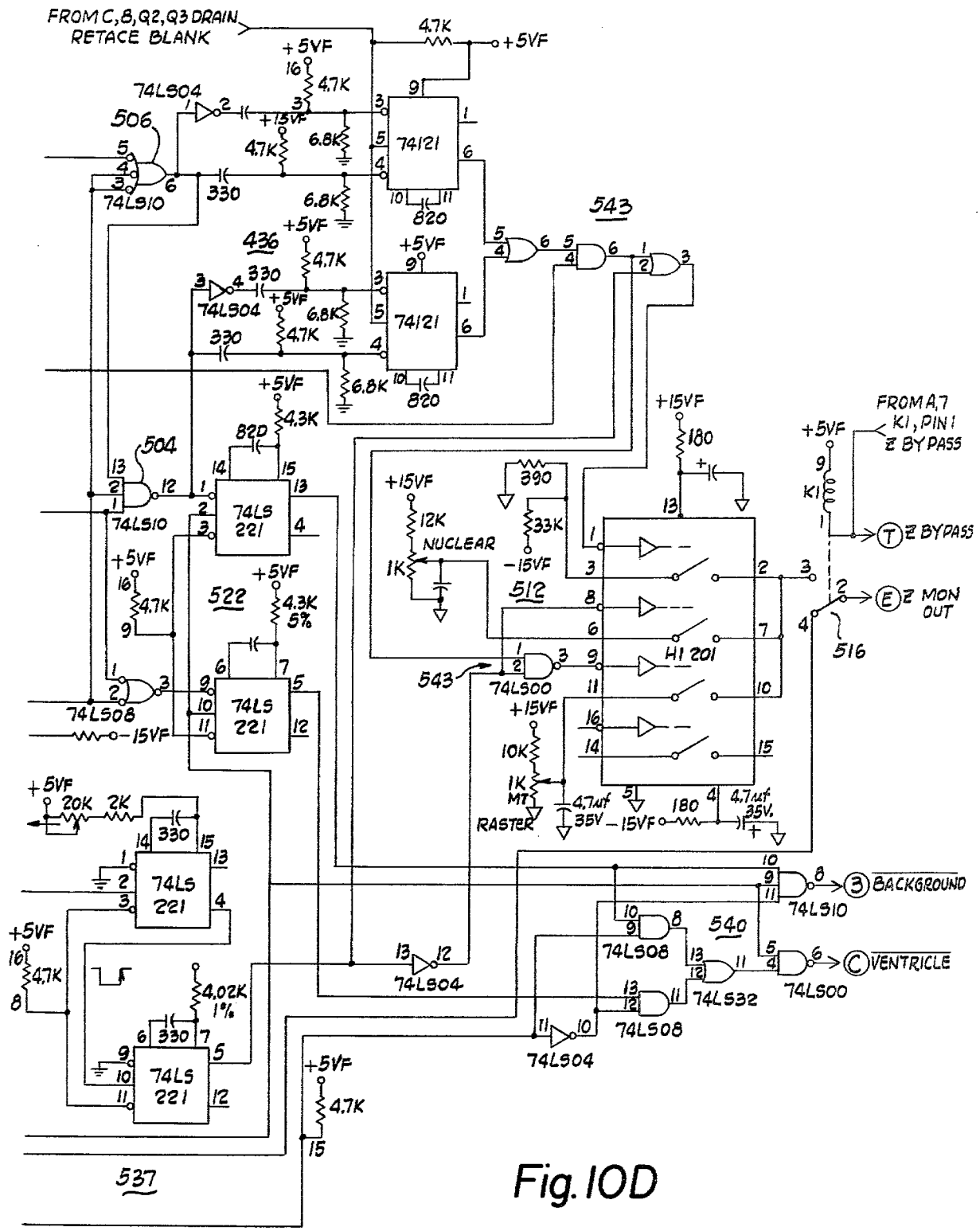

Raster generation is provided by X and Y ramp oscillators 432, 434. (See FIG. 10). The oscillators 432, 434 are free running sawtooth generators whose output produces the raster. During retrace, raster Z one shots 536 are disabled.

Whenever there are no nuclear events to be displayed, the X and Y input signals appearing at the leads 438, 440, respectively, will be at their resting dot levels. Window comparator circuitry 442 will be low, causing analog switch circuitry 444, 446 to route raster ramp signals to the X and Y coordinate terminals of the monitor oscilloscope. When a nuclear event is present, the window comparator 442 goes high, routing nuclear events to the monitor scope through the analog switch circuitry. During display of a nuclear event a MOSFET in the oscillator holds its output constant until the display mode is switched back to raster display, to prevent holes from appearing in the raster. The X and Y raster ramps are summed with their respective joy stick positions in operational amplifiers 450, 452. This allows the raster to be moved over the scope face. The joy stick position information is removed from the raster by operational amplifiers 454, 456, 458 and 460 to keep the displayed regions centered in the raster.

The region of interest display for first pass studies is shaped as shown in FIG. 11.

Figure 11A:
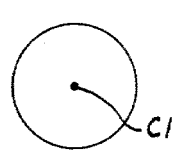
FIGS. 11A–11D are graphical representations of regions of interest electrically defined by the portion of the system shown in FIGS. 9 and 10.
Figure 11B:
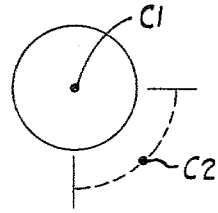
Figure 11C:
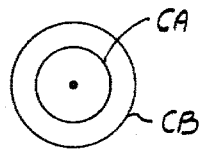
Figure 11D:
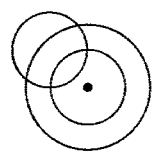

Three circles are used to delineate the region of interest in the first pass mode. The circle in FIG. 11A is a center circle which does not move during rotation of the region of interest. The center of this circle is designated C1. An offset center C2 is located some small distance away from the center C1 (FIG. 11B). This distance is determined by the setting of a "shape" switch SW on the front panel of the cardiac module (See FIG. 1). The offset center C2 can be moved in a path through 90° about the center C1 along the dashed line in FIG. 11B. Around this offset center two different sized concentric circles are delineated, circle CA and circle CB (FIG. 11C).

All three circles are used to shape the region of interest display, but some interior lines are blanked out, leaving an approximate shape of the left ventricle and a horseshoe shaped background region of interest as shown in FIG. 11. When the cardiac module M is in the equilibrium mode, the large translated circle indicated by dotted lines in FIG. 12, is not displayed.

The actual offsetting and rotation of the concentric circles used to define the regions of interest are calculated by other circuitry of the cardiac module described in more detail below, and the results are fed back to the region of interest circuitry 30 as X translate and Y translate signals appearing at the leads 424, 426, respectively.

The calculation of the circumferences of the three circles used to determine the region of interest is as follows: For circle 1 (the stationary center circle) X and Y ramps with joy stick information removed (coming from operational amplifiers 458, 460) are applied to multiplier circuits 462, 464. These multipliers square the ramp voltages. Outputs of the multipliers are summed in an operational amplifier 466 to generate the formula for a circle, X squared plus Y squared. The radius of the first or center circle is determined by size voltage applied to the input of comparator circuitry 468.

To generate the two concentric translated circles (circles CA and CB), the X translate and Y translate signals are summed with the X and Y raster ramps in operational amplifiers 454, 456. The X and Y translate voltages offset the common center of the concentric translated circles and allow this offset center to be translated through 90° around the center C1. Multiplier circuits 470, 472 square the ramp signals (summed already with the translate signals). An operational amplifier 474 sums their outputs. This generates the circle formula as desired. A comparator 476 determines the radius of the smaller translated circle CA, while comparator circuitry 478 determines the radius of the large translated circle CB.

Actual Z unblanking pulses for the region of interest outline display on the monitor oscilloscope are generated in accordance with logic illustrated in FIGS. 13 and 14.

Referring to FIG. 14, a set of Z one shots 436 are required to emit a pulse when any circle circumference line belonging to the region of interest is crossed by a raster ramp signal. A pulse is produced when any of the comparators 468, 478, 476 changes state, in either a positive or a negative direction. The above holds true except where the circle having center C1 intersects the large and small translated circles, as shown in FIG. 13.

All three comparators have high signal outputs when the Y ramp starts its sweep. Refer to the lead 502 in FIG. 13. Three Z pulses must be generated by this ramp signal: First, when the ramp crosses into circle 1; second, when it crosses out of circle CA; and third, when it crosses out of circle CB. As the raster ramp crosses circle 1's comparator reference voltage, (comparator 468) that comparator's output goes low, and both of the outputs of the NAND gates 504, 506 go high, triggering the one shot system 436 for the first Z-pulse.

Transitions from either translated circle are disabled for unblanking as long as the circle 1 comparator 468 retains its low level output. For example, very soon after entering circle 1, the ramp crosses the boundary of circle CB. This causes the output of the circle CB comparator 478 to go low. But since the circle 1 comparator is still low no Z pulse is generated. Before the ramp crosses the boundary of circle 1, it enters circle CA, causing the output of the comparator 476 to go low. Next, the ramp crosses the circle 1 boundary once more, but since both circle CA and circle CB comparators are now low, the low to high transition from the output of the circle 1 comparator cannot change the output of either of the NAND gates 506 or 504, and no Z pulse is generated. Once the ramp leaves the confines of circle 1, its comparator 468 produces a high output, enabling unblanking at transitions from either circle CA or circle CB.

The next defined line which the ramp representation crosses is the circle CA circumference, and, when this happens, the second Z pulse is generated. Finally, the ramp crosses circle CB, and the third Z unblank pulse is thereby generated.

Referring once more to FIG. 13, consider the Y raster line 510. Again, all inputs to both NAND gates 504, 506 are high when the Y ramp starts its sweep. The circle 3 comparator is first to go low, triggering a one shot Z pulse when the output of its NAND gate 504 goes high. This also enables the inputs to the triple input NAND 504 so either of the other two inputs will trigger a one shot when it goes low. Since the circle 1 comparator 468 goes low before the circle CA comparator 476 goes low, a Z one shot is triggered. With circle 1 low, when circle CA goes low, no Z unblank is generated. In such circumstances, the circle 1 comparator goes high, but the circle CA comparator is low, so again no Z unblank pulse is generated in those circumstances. When the circle CB comparator goes high, another Z unblank pulse will be produced.

These Z unblank pulses activate an analog switch 512, removing the minus 1.4 blanking voltage from the oscilloscope and applying a D.C. level in accordance with the setting on a potentiometer 514. The Z unblanking signal appears at a lead 516. When the signal at the lead 518 (FIG. 15) is high, as determined by actuation of a mode select switch 520 (FIG. 1) on the front panel of the cardiac module M, the output of the circle CB comparator is held low, disabling or preventing the generation of a background region definition, since the background region is used only in first pass studies.

While the region of interest outline is being displayed, no nuclear Z pulses from the radiation camera C are processed. A set of radiation count enabled one shots 522 are enabled only when a signal is present on a lead 524 extending to the camera C. Therefore, none of the raster produced Z unblank signals will produce a count indicating on a line 526, 528, that a particular count corresponds to radiation within the background and central, or ventricle, region of interest, respectively.

The X-Y coordinates of nuclear events are buffered by operational amplifiers 530, 532. The size of the nuclear image can be varied in X-Y gain, from 1 to 1 to approximately 2 to 1 by variable amplifiers 534, 536. Gain is controlled by varying the D.C. voltage of a set of operational amplifiers 999 and 998, with the degree of a signal impressed on a lead 540, as controlled by a potentiometer 542 on the front panel of the cardiac module M (FIG. 1). Further amplification is obtained in operational amplifiers 997 and 996.

Nuclear event count representations are also transmitted for representation on the monitor oscilloscope. When a nuclear event is represented on the output of the Y buffer amplifier 532, the window comparator 442 goes high, routing nuclear event representation to the monitor scope through the analog switching circuitry 444, 446. Nuclear data can then pass through the same circuitry as described in connection with the raster display information, except that information produced by the joy stick J is no longer removed from the nuclear data going to the multipliers 464, 462.

Thus, the raster image moves on the scope but dots representing nuclear events do not. However, the correct nuclear event information is counted by offsetting them exactly the same amount as the joy stick position indicates before they go through the circle comparators.

Decoding of nuclear events into indications of radiation within the ventricle (central) and background region of interest, respectively, is accomplished with the same comparator system as with the raster display. Only the leading edge of each pulse representing a nuclear event is detected. The outputs of the circle comparators disable or enable the counting one shots, depending on whether the X and Y nuclear event information indicate an event lying outside of, or within, a delineated central or background region of interest. Nuclear events within the delineated background region but not within the central region cause the inverting input of a background one shot in the set 522 to go low, enabling the one shot. Nuclear events within the ventricle region cause the inverting input of the ventricle one show within the set 522 to go low, enabling that one shot. Nuclear events within the ventricle region cause the inverting input of the ventricle one shot 522 to go low, enabling that one shot.

The Y window comparator 422 output, which routes nuclear events to the monitor scope, also triggers the one shot 995. This disables the output of the Z raster one shots 436 from smearing nuclear events on the monitor oscilloscope. Nuclear monitor Z signals from the nuclear camera C are delayed by one shot circuitry 537 to be synchronized with the coordinate signals that are delayed by propagation through the analog section of this system.

The one shot 522 fires on the trailing edge of the nuclear camera monitor Z signal, to ensure stabilization of the region's comparators before the ventricle/background one shots 540 are triggered. Once triggered, these one shots are immune to any further noise from the region of interest comparators. ANDing the first one shot with the count enable one shots 522 ensures that only one pulse indicating ventricle (central region) or background occurs per each nuclear event signalled by the nuclear camera C.

When calculating ejection fraction, the signal at the lead 542 is low, and the "ventricle" and "background" pulses are routed to their appropriate outputs, i.e., leads 526, 528. Background mode is used to isolate and verify background counts in a taped first pass study. This facilitates setting up the regions of interest for the first pass studies from tape. When in the background mode, so-called ventricle pulses at the lead 528 are disabled and "background" pulses at the lead 528 are disabled.

"Background" pulses at the lead 526 are routed through the "ventricle" output 528 to be counted. "Bypass" signals, appearing at a lead 994, bypass X, Y and Z signals from the nuclear camera around the cardiac module M when the signal at the lead 994 is high. Turning off A.C. power to the cardiac module also bypasses the module.

FIGS. 10A–10D show the region of interest circuitry in schematic form.

THE SUBTRACTION AND BACKGROUND CIRCUITRY 32

The subtraction and background circuitry includes four general sections. Included is a "not ready" sequence circuit 600 (FIG. 16), region of interest rotation circuitry 602 (FIG. 15), subtraction and constant background circuitry 604, and a self-test unit 44.

The "not ready" sequencing circuitry 600 initiates the operation of the cardiac module M after the receipt of two R peak signals over a lead 608 and one "carry" signal over a lead 610. The two R peak signals are needed for calibration of image pulses. The "not ready" sequence consists of three RS flip-flops. When a "start" signal appears at a lead 612, it causes the three flip-flops of the circuitry 600 to change state. The first two go low, and the third goes high, causing the system to clear the 256×12 memory 38 of the ejection fraction calculation circuitry 40. The first R peak signal sets the first flip-flop, which enables the second. When the second flip-flop receives a "carry" pulse over the lead 610 from the ejection fraction calculation circuitry, it enables the third flip-flop. Any more than one "carry" pulse may occur during this time, but only one is needed to advance the "not ready" sequencer. When the next R peak signal occurs on the lead 608, the "not ready" sequencer goes low and initiates the study by the cardiac module M.

Figure 17:
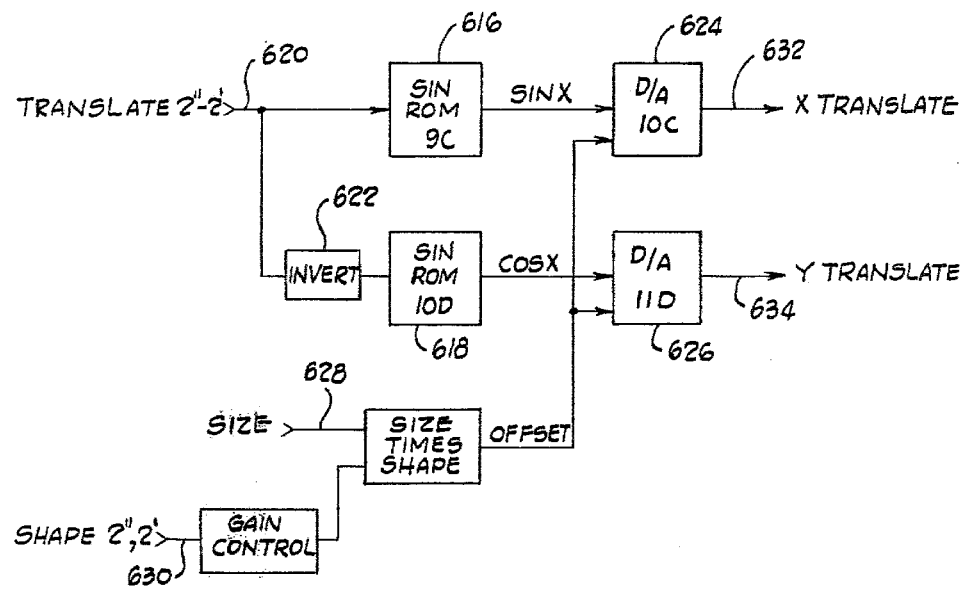
FIG. 17 is another detailed block diagram illustrating another portion of the system of FIG. 2.

Rotation and changes of shape of the region of interest are accomplished by offsetting the concentric circles (two offset circles (CA and CB) in first pass, and one offset circle in equilibrium mode, by means of a D.C. voltage proportional to the size of the circle times one of three possible fixed gains determined by the shape bits. The circuitry in the subtraction and background circuitry takes the four translate rotation bits from the front panel circuitry and converts them to a sine X and cos X set of signals (where X is the rotation angle). Refer to FIG. 17.

Both sine X and cos X are obtained from sine table ROM's 616, 618. Since cos X equals sine (90°-X) the complement of the binary translate angle, expressed by the signal on a lead 620 when input to the sine table ROM, will yield cos X.

Having passed through an inverter 622, the ROM outputs are fed into digital to analog converters 624, 626 where the magnitudes of the sine X and cos X outputs are controlled by both the "size input", on the lead 628, and the shape input, on the lead 630. The digital to analog converter translate output, from the lead 620, is converted from current to voltage, and sent to the region of interest delineation circuitry as "X" translate and "Y" translate signals, on leads 632, 634.

Figure 18:
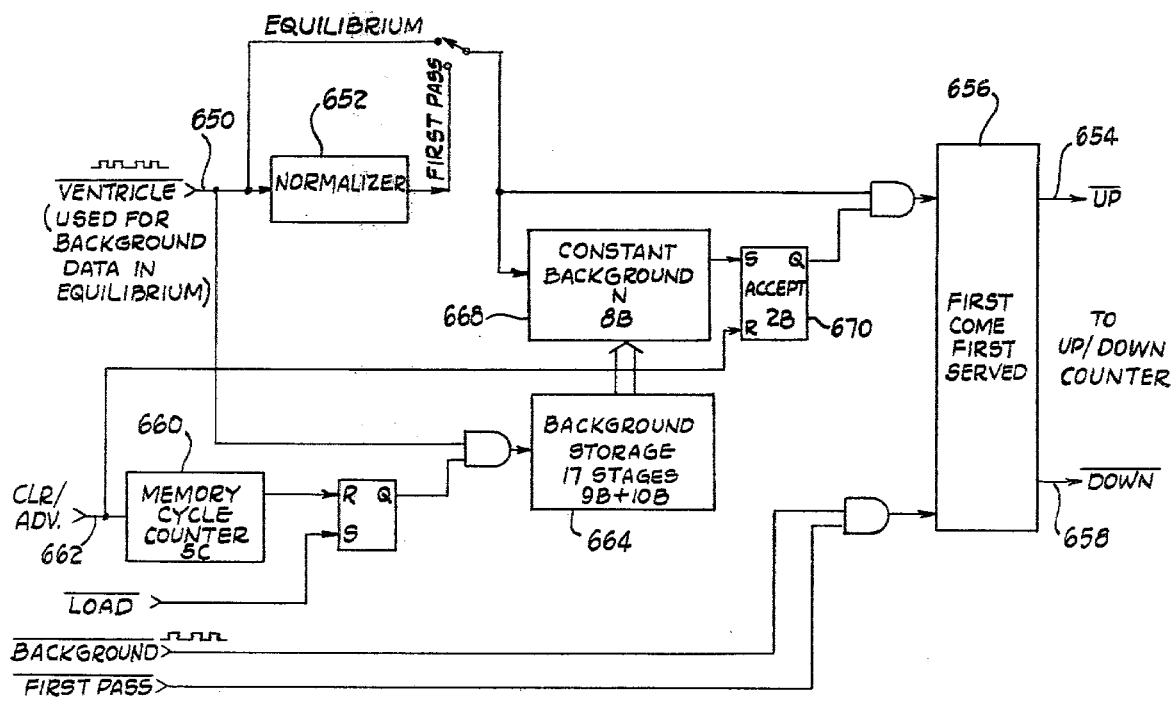
FIG. 18 is another detailed block diagram illustrating another portion of the system of FIG. 2.

The subtraction of the background signals from the "ventricle", or central region of interest, signals, is done in two ways depending upon the type of study performed. Refer to FIG. 18. If the study is done in the "first pass" mode, i.e., the collection of data begins almost with the injection of the bolus, the background is sampled and subtracted during each and every subinterval of the patient's heartbeat. The up/down counter 38 referred to above in connection with the ejection fraction calculation circuitry 40, performs the subtraction. Background data is supplied to the "down" input of the up/down counter. Up counts (central region of interest data), appearing at a lead 650, are scaled by a normalizer circuit 652 which makes the horseshoe shaped background area and the central ventricle area "look" equal in size. Normalized ventricle counts are sent to the "up" input of the up/down counter in the ejection fraction calculation circuitry 40. This input appears in FIG. 18 as a lead 654. A "first come first served" circuit 656 insures that there is no data present on both the up input and down input (658), at the same time.

In the event that the study is done in the so-called "equilibrium" mode (i.e., one-half hour or so after the bolus injection), the background is stored before the study starts and subtracted from the ventricle data at the beginning of each heartbeat subinterval. In this mode, background to be stored goes into the subtraction and background circuitry 32 through the input 650. For good statistics, the background is sampled for 512 memory cycles of the memory 38, and the average of that number is stored as the background in equilibrium mode. A memory cycle counter 660 counts the 512 memory cycle intervals by counting the signals on the lead 662, which originate at 993. A background dividing counter 664 is 24 stages long but only 17 stages are used. This counter stores all the background counts for 512 memory cycles. Its output is the average of the 512 memory cycles. The average is calculated by shifting the number stored into the counter by 9 bits, e.g., by using the output stages 10 through 17.

At the beginning of each heartbeat subinterval, the background value stored is fed into the constant background divided counter 668. A set of flip-flop gates 670 gates the central region of interest data not to reach the first come first served circuitry 656. In the same time, the ventricle data clocks the constant background counter 668 which counts down from the preset value (which is the stored background value) to zero. It then sets the flip-flops 670, and in response thereto, ventricle data is enabled to reach the circuitry 656. In effect, the data reaching the circuitry 656 is the input ventricle (central region) data, minus the stored average background value. All counters in the constant background circuitry 668 are cleared when the front panel switch 672 ("load") is depressed.

Figure 19:
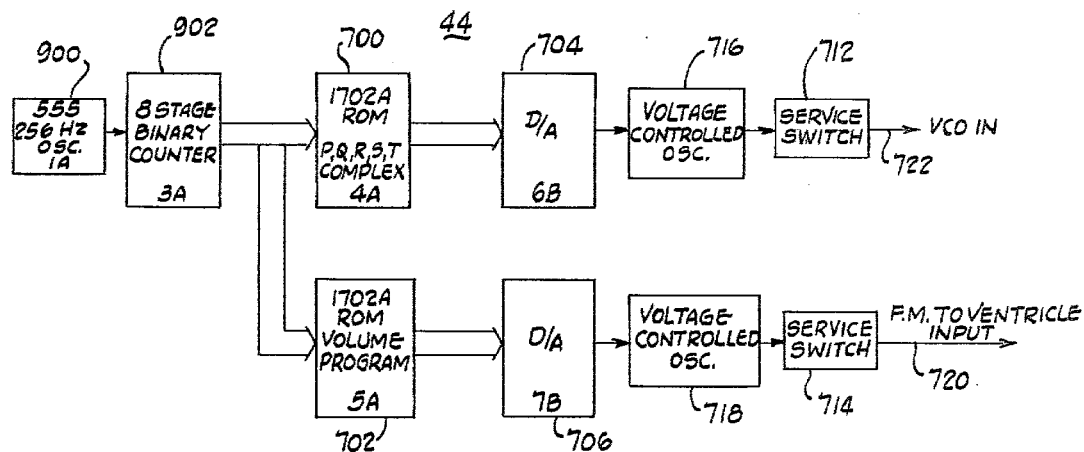
FIG. 19 is a block diagram illustrating another portion of the system of FIG. 2.

The test unit is illustrated in detailed block form in FIG. 19. In order to test the cardiac module M, patient's heart data is simulated. Digital representations of an ECG signal and of nuclear central region of interest activity data are stored in two ROM's 700, 702. To synchronize the cardiac module memory 38 for testing purposes, both ROM's 700, 702 are continually sequentially addressed, simulating a heart rate of 60 beats per minute. The digital outputs of the ROM's 700, 702 are converted to analog signals by digital-to-analog converters 704, 706. Special service switches 712, 714 control the routing of these simulated test waveforms into the functional circuitry of the cardiac module, after processing by voltage controlled oscillators 716, 718. The ECG waveform is converted to a frequency modulated (FM) signal by the voltage controlled oscillator 718 and sent to the demodulating circuit 78 (See FIG. 3)

downstream from the ECG isolation amplifier over a lead 720. This operation tests almost all the R-wave and memory timing circuitry. The volume curve waveform is converted to a representative nuclear activity by sweeping a voltage controlled oscillator 716. This FM output is sent to the "ventricle" input testing the subtraction and background circuitry and ejection fraction calculation circuitry, by way of a lead 722.

The subtraction and background circuitry is illustrated in schematic form in FIGS. 15A-15D. The three flip-flop circuits in the subtraction and background circuitry are shown generally at 800 in FIG. 15C. When a signal is applied at a lead 802, the flip-flop 804 is reset. This resets the flip-flop 806, which in turn resets the flip-flop 808 and the signal at the lead 810 ("not ready") goes high. When the signal on a lead 812 goes low, the flip-flop 804 is set. This allows a subsequent signal on a lead 814 to set the flip-flop 806. On the next occurrence of a apulse at the lead 812, the flip-flop 808 is reset and the signal at the lead 810 goes low.

Figure 15A:
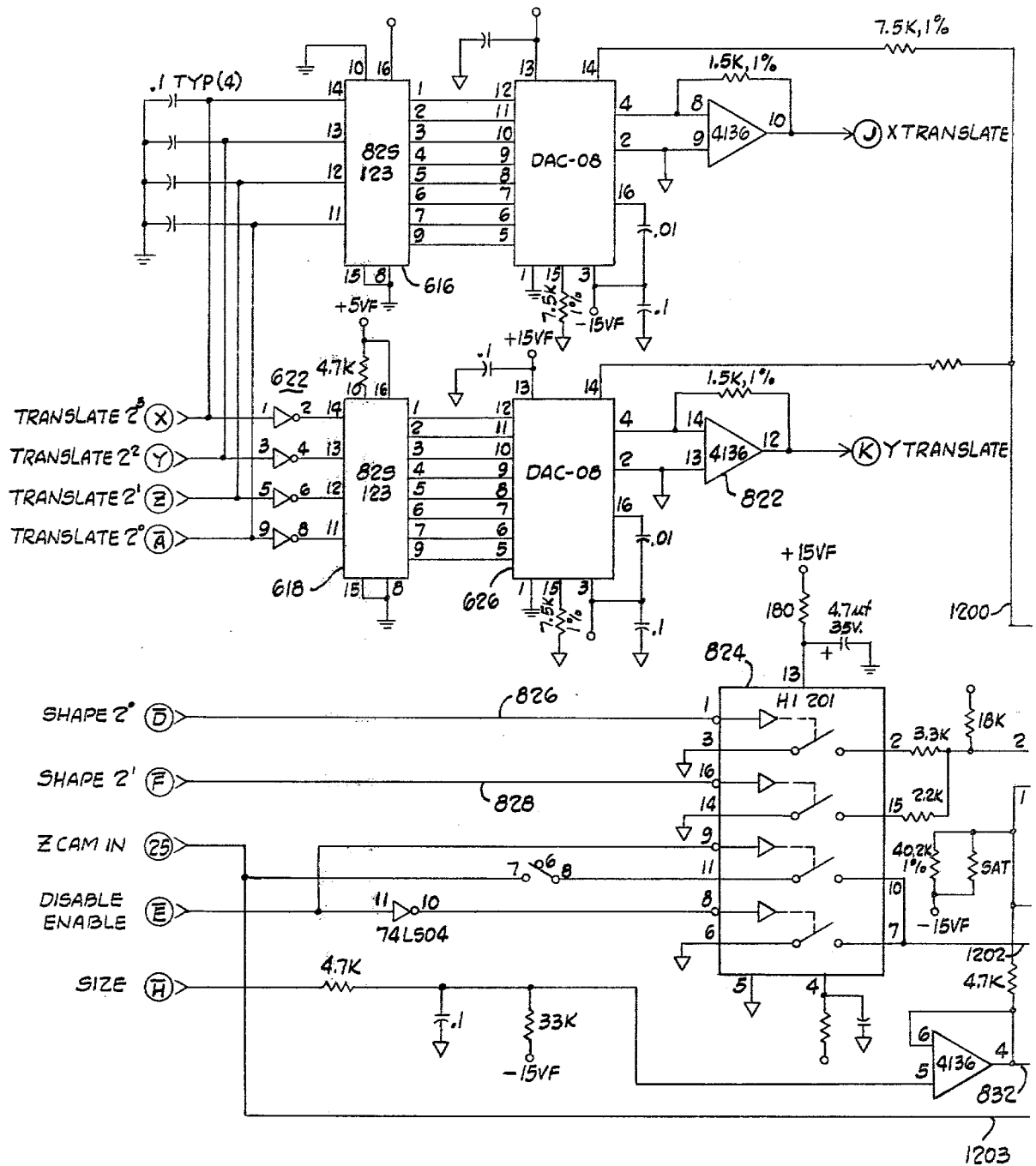
FIGS. 15A–15D are schematic drawings of the portion shown in FIG. 15.
Figure 15B:
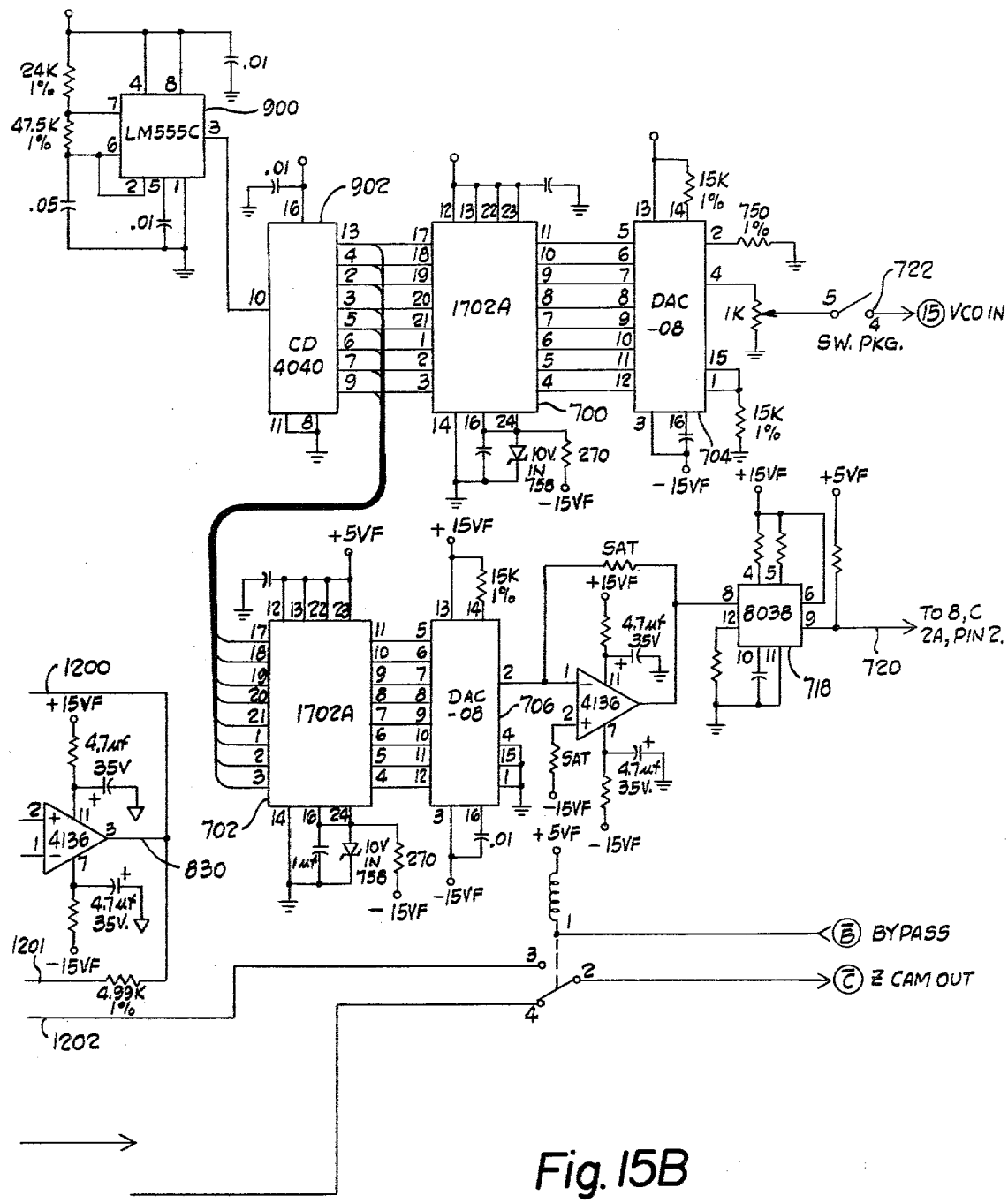

Referring to FIG. 15A, the signals appearing at a set of leads 818 represent in binary the desired rotation angle for the region of interest, as established by the pot 520 on the front panel of the cardiac module M. This angle is fed into the sine table ROM 616. It is also inverted in the set of inverters 622 and fed to the second sine table ROM 618. The inputs into the digital to analog converters 624, 626, are sine X and cos X. Amplitude is controlled by an amplifier 822.

Switching circuitry 824 serves two purposes. First of all the signals at the leads 826 and 828 control the output signal appearing at the output 830. This controls the shape of the region of interest displayed, by setting the reference current of the digital-to-analog converters 654, 626. The other half of the switching circuitry 824 controls the Z signal to the nuclear camera oscilloscope. An amplifier output appearing at a lead 832 is summed into the signal at the lead 830, so that no change in shape occurs when the "size" of the region of interest is adjusted.

The state of the leads 826, 828, as input to the switching circuitry 824, are a binary representation of the shape of the region of interest, set as desired by an appropriate setting on a switch 838 on the front of the control panel of the cardiac module M.

Figure 15C:
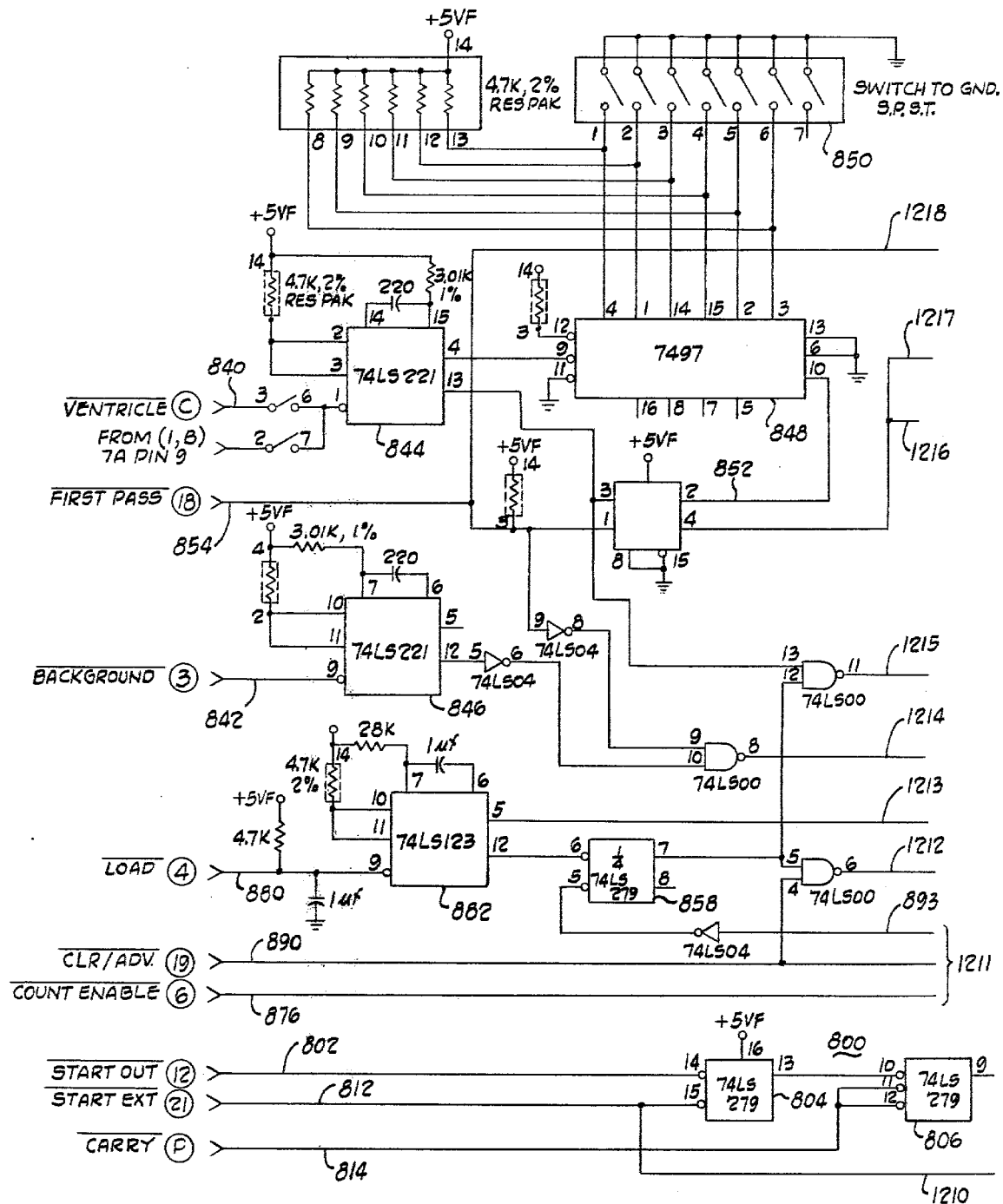
Figure 15D:
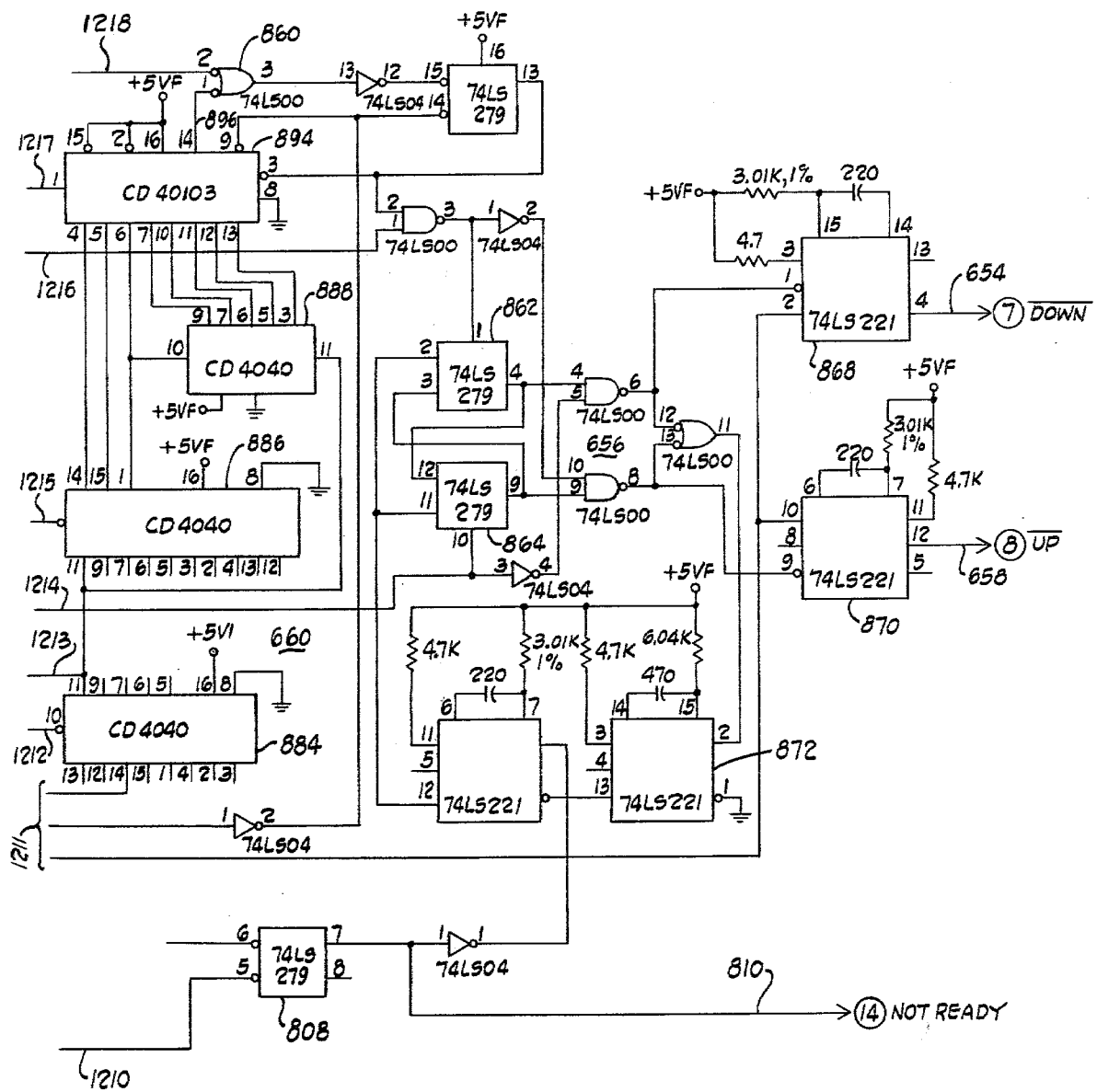

The counting logic of the subtraction and background circuitry is illustrated in FIGS. 15C and 15D. In the first pass mode, signals appear at the lead 840 (ventricle or central region signals) and at the lead 842 and proceed to circuits 844, 846. The circuitry 844, 846 converts these input pulses into 200 nanosecond (ns) pulses. The ventricle pulses then proceed to the circuit 848 which is programmed by a switch 850 to correct for size differences between ventricle and background information. The scaled ventricle counts appear at a lead 852. When the signal at the lead 854 is low, indicating a first pass mode of operation, the scaled ventricle counts pass to a lead 856. The flip-flop 858 is held set so the ventricle information proceeds through an OR gate 860. Circuits 862, 864 make up the first come first served network 656. The first to occur of a ventricle or a background pulse will lock out the other, so the output one shots 868, 870 cannot fire at once. A one shot 872 serves to reset the first come first served network 656 for the next pulse. A signal at the lead 876 prevents output pulses during memory transfers.

In the equilibrium mode, the signal at the lead 854 is high. In such a circumstance, the scaler 848 is not used and the input at the lead 842 is disabled. When a signal at the lead 880 is sensed by the circuit 882, a reset signal is generated which resets counter circuitry 884, 886, 888. Then circuitry 884 counts for 512 memory cycles, represented by pulses occurring on a lead 890. During this time the counter circuitry 886, 888 counts the background activity from the input 840 (this is for loading the background sample); the region of interest is set over a background region at this time.

After 512 channels are counted the signal at a lead 893 goes high, enabling the clock input to counting circuitry 884, 886. The output of the counting circuitry 886 and 888 is shifted 9 bits (divided by 512) and fed as the input to a dividing counter circuit 894. This number remains in the counting circuitry 886, 888 throughout the study, and until the recurrence of a signal at the lead 880. The dividing counter 894 is loaded with the constant background number in response to each pulse on the lead 890. In response to such a pulse, the flip-flop 858 is also reset, disabling the gate 860 so that no ventricular pulses can pass.

The dividing counter 894 counts ventricle pulses until it has counted a predetermined N pulses, at which time the signal at the lead 896 goes low. The number N, of course, is the number of background average pulses established by the counting circuitry 886, 888. When the signal at the lead 896 goes low, this allows ventricle pulses to pass for the remaining time until the next pulse appears at the lead 890.

A test generator 900 is shown in FIG. 15D and FIG. 19. The test generator 900 drives a 12 bit counter 902 which addresses the 256 X4 ROMs 700, 702. The ROM 700 has for its program a digital representation of a typical ECG waveform which is converted to a voltage through the digital analog converter 704, and then converted to a frequency modulated signal by a voltage controlled oscillator. The ROM 702 has a typical volume curve of the heart as its program, which is converted to a voltage through the digital-to- analog converter 706, and then converted to a frequency in the voltage controlled oscillator 718.

The cardiac module M is suitably embodied by a product "Cardiac Module" manufactured by Picker Corporation, Northford, Connecticut, U.S.A.

It is to be understood that this disclosure is illustrative, rather than exhaustive, of the invention described here. Persons of ordinary skill may make certain additions, deletions or alterations to the preferred embodiment described here without departing from the spirit or scope of the invention, as described in the appended claims.

What is claimed is:

1. A cardiac function evaluating system utilizing radiation event counts from a radioisotope in the cardiovascular system of a subject, the system comprising:
   (a) a radiation detector for producing data describing radiation count location distribution of the radioisotope in the subject over a two dimensional field;
   (b) circuitry for electrically segregating said data corresponding to radiation events occurring within a predetermined electronically defined region of interest within the field and encompassing a portion of the subject's hear to be evaluated, said electrical segregation being executed in real time relative to the production of the data;
   (c) time gated multichannel memory circuitry for processing said segregated data for evaluating a heart function, and (d) display apparatus responsive to the time gated memory circuitry for producing an indication of a characteristic of the heart function being evaluated.

2. The system of claim 1, wherein the time gated memory circuitry comprises circuitry for substantially defining a curve representing a time variation of the quantity of blood within the portion of the subject's heart.

3. The system of claim 2, wherein said memory circuitry comprises means for defining said curve by a sequence of radiation count totals each corresponding to one of a sequence of time subintervals of a heartbeat cycle.

4. The system of claim 3, wherein each of said time intervals is approximately 5 milliseconds in duration, the sequence having approximately 256 each subintervals.

5. The system of claim 3, further comprising circuitry for adjusting the duration and number of said subintervals of the heartbeat cycle.

6. The system of claim 1 where the data segregating circuitry comprises means for defining said region of interest as a pair of overlapping circles approximately representing an ellipse.

7. The system of claim 1, further comprising:
means for adjusting the size, shape, relative position and orientation of said region of interest.

8. The system of claim 1, further comprising:
circuitry for defining a second region of interest.

9. The system of claim 8, further comprising:
circuitry for subtracting radiation counts correspond to radiation occurring within the second region of interest from those corresponding to said region of interest.

10. The system of claim 9, wherein said subtracting circuitry performs said subtraction in real time.

11. The system of claim 9,
(a) further comprising; memory circuitry for storing the number of counts corresponding to said second region of interest, and
(b) wherein said subtraction circuitry subtracts the counts from the second region of interest from those of the first region of interest periodically.

12. The system of claim 8, wherein:
(a) said region of interest is defined as at least a first circle, and
(b) said second region of interest is defined as at least a portion of an annulus defined by a second circle concentric with said first circle.

13. The system of claim 12, wherein:
(a) said first region of interest is defined by first and second overlapping circles; and
(b) said second region of interest is defined by portions of annuli defined by two circles concentric with said first and second circles.

14. A method for evaluating cardiac function utilizing radiation unit counts from a radioisotope in the cardiovascular system of a subject, said method comprising the steps of:
(a) producing data describing radiation count location distribution of the radioisotope in the subject over a two dimensional field;
(b) electrically segregating said data corresponding to radiation events occurring within a predetermined region of interest within the field and encompassing a portion of the subject's heart to be evaluated, said segregation step being performed in real time;
(c) processing the segregated data for evaluating a heart function, and
(d) producing an indication of a characteristic of the heart function being evaluated in response to the data processing.

15. The method of claim 14, wherein the processing step comprises:
defining a curve representing a time variation of the quantity of irradiated blood within the portion of the subject's heart corresponding to the region of interest.

16. The method of claim 15, wherein said defining step comprises defining said curve by a sequence of radiation count totals each corresponding to one of a sequence of time subintervals of a heartbeat cycle of the subject.

17. The method of claim 16, wherein said defining step further comprises:
adjusting the duration and number of said subintervals.

18. The method of claim 14, wherein said region of interest defining step comprises:
defining the region of interest by a pair of overlapping circles approximately representing an ellipse.

19. The method of claim 18, wherein said region of interest defining step further comprises:
adjusting the size, shape, relative position and orientation of said region of interest.

20. The method of claim 14, further comprising the step of:
defining a second region of interest.

21. The method of claim 20, further comprising the step of:
subtracting radiation counts corresponding to radiation events occurring within the second region of interest from those corresponding to events within the region of interest.

22. The method of claim 21, wherein:
said subtracting step is executed in real time.

23. The method of claim 21, wherein:
(a) said method further comprises the step of storing radiation counts corresponding to said second region of interest, and
(b) wherein said subtraction step is executed periodically by use of the stored radiation counts corresponding to the second region of interest.

24. The method of claim 20, wherein:
(a) said region of interest defining step defines a region of interest by at least a first circle, and
(b) said second region of interest defining step comprises defining at least a portion of an annulus described by a second circle concentric with the first circle.

25. The method of claim 20, wherein:
(a) said first region of interest defining step comprises defining the first region of interest by means of first and second overlapping circles, and
(b) said second region of interest defining step comprises defining said second region of interest by portions of annuli each defined by one of two circles concentric with said first and second circles.

26. The method of claim 14, further comprising the step of:
discarding stored radiation count information representing a predetermined portion of the heartbeat cycle of the subject.

27. A nuclear cardiology system for use in connection with a scintillation camera for evaluating the cardiac function of a patient vascularly injected with a radioactive tracer, the camera producing counts each describing the location of a radiation event caused by the presence of the tracer in the patient's body, said nuclear cardiology system comprising:
   (a) means for defining a region of interest of the patient's body;
   (b) discrimination circuitry for selecting, in real time, radiation count signals corresponding to radiation events within the region of interest;
   (c) circuitry for dividing the patient's heartbeat cycle into a series of time subintervals synchronous with the patient's electrocardiogram;
   (d) a multichannel memory for accumulating an indication of the number of counts corresponding to the region of interest during each of the subintervals;
   (e) calculating circuitry for scanning the information stored in the multichannel memory for determining the maximum and minimum count values accumulated in the memory channels, and
   (f) means responsive to the calculating circuitry and the multichannel memory for producing a representation of a characteristic of the patient's heart function.

28. The system of claim 27, wherein:
   (a) said region of interest defining means comprises circuitry for defining a region of interest substantially isolating the patient's left ventricle, and
   (b) said calculating circuitry comprises means for calculating the ejection fraction of the left ventricle.

29. The system of claim 27, further comprising:
   circuitry coupled to the multichannel memory for rejecting information in a predetermined portion of said memory channels prior to calculation.

30. The system of claim 29, wherein said rejection circuitry comprises:
   circuitry for rejecting information in those memory channels representing subintervals comprising approximately the final 25% of the patient's heartbeat cycle.

31. A nuclear cardiology method for employment in connection with a scintillation camera for evaluating the cardiac function of a patient vascularly injected with a radioactive tracer, the camera producing counts each describing the location of a radiation event caused by the presence of the tracer in the patient's body, said method comprising the steps of:
   (a) defining a region of interest of the patient's body;
   (b) selecting, in real time, radiation count signals corresponding to radiation events within the region of interest;
   (c) dividing the patient's heartbeat cycle into a series of time subintervals synchronous with the patient's electrocardiogram;
   (d) accumulating an indication of the number of counts corresponding to the region of interest during each of the subintervals;
   (e) scanning the information stored in the multichannel memory for determining the maximum and minimum count values accumulated in the memory channels, and
   (f) producing a representation of a characteristic of the patient's heart function in response to the calculation.

32. The method of claim 31, wherein:
   (a) said region of interest defining step comprises defining a region of interest substantially isolating the patient's left ventricle, and
   (b) said calculation step comprises calculating the ejection fraction of the left ventricle.

33. The method of claim 31, further comprising the step of:
   rejecting information in a predetermined portion of said heartbeat cycle.

34. The method of claim 33 wherein said rejection step comprises:
   rejecting information representing subintervals comprising approximately the final 25% of a heartbeat cycle of the patient.

35. A system for evaluating cardiac function of an animal body containing a radioactive tracer substance, the system being for use in connection with apparatus for producing radiation count signals each indicating the occurrence and location of a radiation event within the animal body, and for use with electrocardiogram apparatus, said system comprising:
   (a) means for defining a spatial region of interest of the body;
   (b) means for identifying radiation counts produced in response to radiation events within the region of interest;
   (c) circuitry for:
      (i) discarding radiation counts produced in response to events occurring outside the region of interest, and
      (ii) discarding information relating to the location of radiation events occurring within the region of interest; without storage of the discarded information;
   (d) time gating circuitry synchronized with an electrocardiogram of the body for dividing the heartbeat interval of the body into a series of time subintervals;
   (e) a multichannel memory system for accumulating in each of its respective channels the number of radiation counts corresponding to the region of interest during a different one of the respective heartbeat time subintervals, and
   (f) circuitry for employing the counts stored in the multichannel memory for generating an indication representing a characteristic of cardiac function of the animal body.

36. A method for evaluating cardiac function of an animal body containing a radioactive tracer substance, the method being for use in connection with apparatus for producing radiation count signals, each count signal indicating the occurrence and location of a radiation event within the animal body, and for use with electrocardiogram apparatus, said method comprising the steps of:
   (a) defining a spatial region of interest of the body;
   (b) identifying radiation counts produced in response to radiation events within the region of interest;
   (c) discarding radiation counts produced in response to events occurring outside the region of interest, and also describing location information relating to radiation events occurring within the region of interest, said discarding being carried out without storage of the discarded information;
   (d) dividing the heartbeat interval of a body into a series of time subintervals;
   (e) accumulating in each of a plurality of channels the number of radiation counts corresponding to the region of interest and occurring during a different one of the respective subintervals, and
   (f) employing the stored counts for generating an indication representing a characteristic of cardiac function of the animal body.

* * * * *

UNITED STATES PATENT AND TRADEMARK OFFICE
CERTIFICATE OF CORRECTION

PATENT NO. : 4,245,646

DATED : January 20, 1981

INVENTOR(S) : BASIL N. IOANNOU et al

It is certified that error appears in the above-identified patent and that said Letters Patent are hereby corrected as shown below:

Figure 3, should appear as per attached.

Applicant/Inventor, 2 occurrences, "Basil N. Ionnou" should be --Basil N. Ioannou--;
Column 4, line 44, "hart" should be --heart--;
Column 12, line 7, "262" should be --264--;
Column 14, line 63, before "peak" insert --R--;
Column 15, line 1, "pin" should be --pins--;
Column 22, line 63, "hear" should be --heart--;

UNITED STATES PATENT AND TRADEMARK OFFICE
CERTIFICATE OF CORRECTION

PATENT NO. : 4,245,646                              Page 2 of 2

DATED       : January 20, 1981

INVENTOR(S) : BASIL N. IOANNOU et al

It is certified that error appears in the above—identified patent and that said Letters Patent is hereby corrected as shown below:

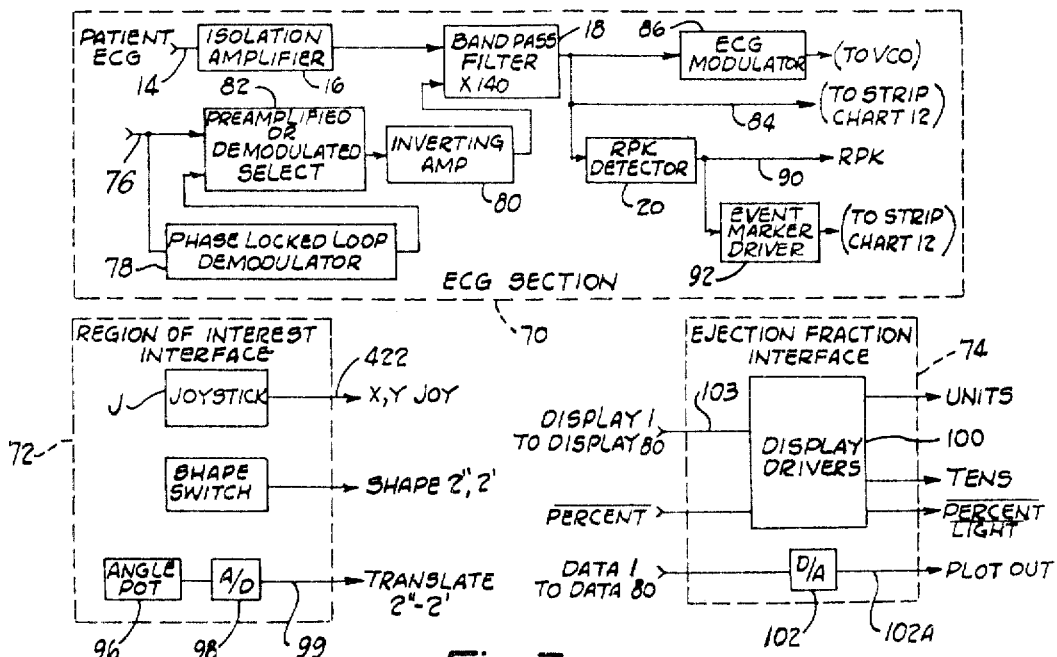

Fig. 3

Signed and Sealed this

Fourteenth Day of July 1981

[SEAL]

Attest:

Attesting Officer

GERALD J. MOSSINGHOFF

Commissioner of Patents and Trademarks